United States Patent [19]
Shields et al.

[11] Patent Number: 6,033,627
[45] Date of Patent: Mar. 7, 2000

[54] BEVEL CLOSURE ASSAY DEVICE HOUSING

[75] Inventors: Ernest David Shields, San Jose; Joyce Lee Norell, Ben Lomond, both of Calif.

[73] Assignee: SmithKline Diagnostics, Inc., Fullerton, Calif.

[21] Appl. No.: 08/971,705

[22] Filed: Nov. 17, 1997

[51] Int. Cl.[7] .................................................. G01N 33/48
[52] U.S. Cl. .............................. 422/58; 422/61; 422/102
[58] Field of Search ................................ 422/56, 58, 61, 422/102

[56] References Cited

U.S. PATENT DOCUMENTS

| | | |
|---|---|---|
| 1,926,299 | 9/1933 | Monk . |
| 3,078,031 | 2/1963 | Kauffeld . |
| 3,122,301 | 2/1964 | Barr . |
| 3,307,770 | 3/1967 | Wysocki . |
| 3,951,332 | 4/1976 | Torbeck . |
| 4,225,557 | 9/1980 | Hartl . |
| 4,285,461 | 8/1981 | Meyers . |
| 4,464,552 | 8/1984 | Pawlowski . |
| 4,789,629 | 12/1988 | Baker et al. . |
| 4,803,048 | 2/1989 | Nason . |
| 4,960,565 | 10/1990 | Shurben . |
| 4,976,354 | 12/1990 | Levy et al. . |
| 5,024,323 | 6/1991 | Bolton . |
| 5,100,619 | 3/1992 | Baker et al. . |
| 5,106,582 | 4/1992 | Baker . |
| 5,119,941 | 6/1992 | Lepie . |
| 5,143,210 | 9/1992 | Warwick et al. . |
| 5,308,580 | 5/1994 | Clark . |
| 5,441,698 | 8/1995 | Norell . |
| 5,468,648 | 11/1995 | Chandler . |

*Primary Examiner*—Lyle A. Alexander
*Attorney, Agent, or Firm*—William H. May; P. R. Harder; Merchant & Gould

[57] ABSTRACT

A closure and a device for use with a closure are described. The closure includes a first member having an interrupted beveled edge, a second member having an undercut edge, and optionally a base member to which the second member is fixed. The first member is adapted to be received with the interrupted beveled edge retained by the undercut edge. A test device can include such a closure and can also include a hinge between the first and second members. Test elements, such as a chromatographic medium, an absorber, an applicator, or a sample application zone, can be disposed on the first member and/or the base member and can be brought into opposition by closing the first member with the closure. The beveled edge is interrupted by one or more uncut portions or bridges. A testing device according to the present invention can perform a number of types of immunoassays, including unidirectional assays, bidirectional assays, and assays employing a split flow path.

109 Claims, 15 Drawing Sheets

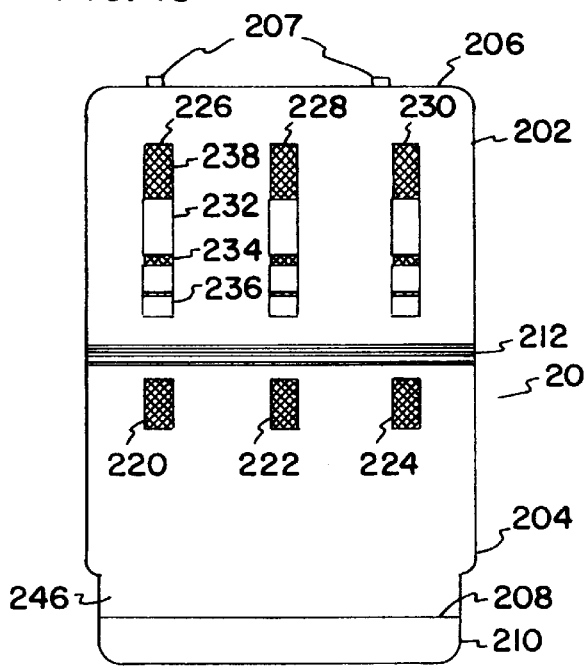
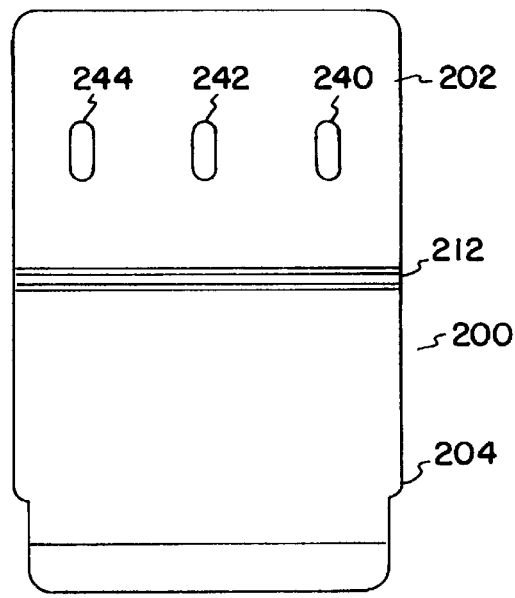
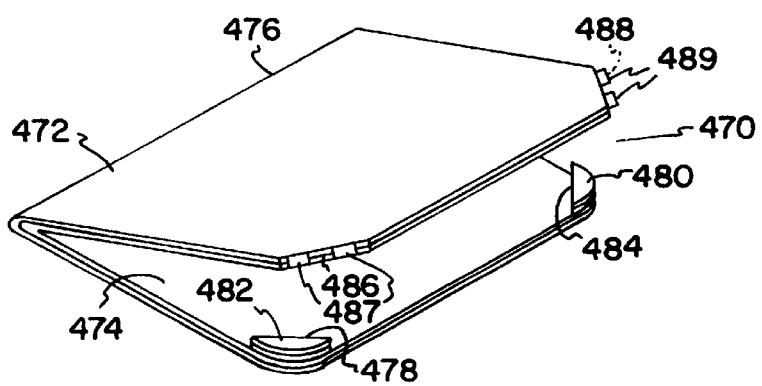

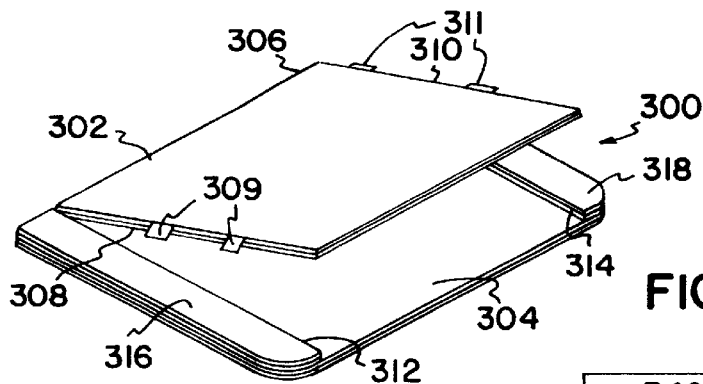
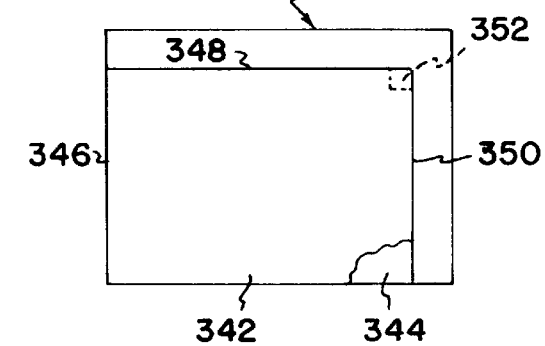
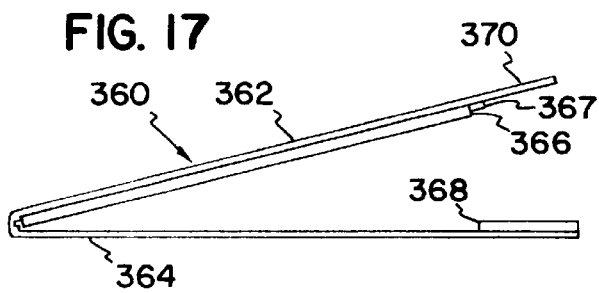
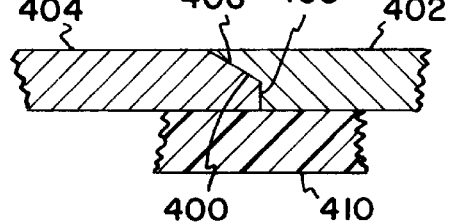
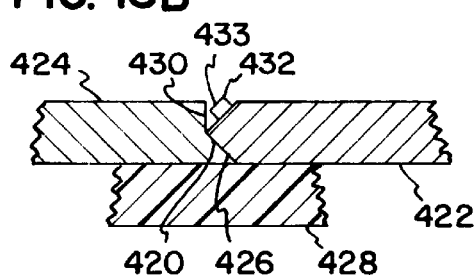
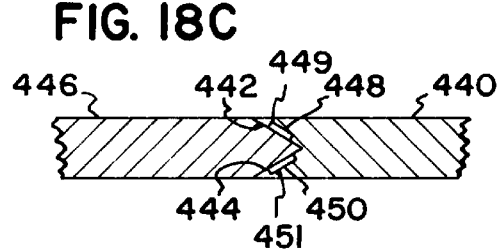

BEVEL CLOSURE ASSAY DEVICE HOUSING

BACKGROUND OF THE INVENTION

The present invention is directed to the field of closures and devices using such closures, particularly testing devices for testing for analytes of biological interest.

Various closure devices are known in the art for closing test devices and require a flap or cover to be closed over a base portion of the test device. One simple example is a transfer adhesive that is applied to the base and covered with a peelable tape. The tape is removed and the flap is then pressed against and retained by the adhesive. Typically, however, the adhesive will not thereafter release the flap, so that the flap may not be again opened without destroying the transfer adhesive closure. Although resealable adhesives do exist, these adhesives are typically not strong enough for use in such devices.

If the flap is to be closed more than once, previously known closure techniques include peelable adhesives carried by a length of tape that is applied over the flap and base. The tape may be peeled back to open the flap and then reapplied to reclose the flap. Additional examples of closure techniques includes hook-and-loop fasteners and snap fasteners, where one element of such a fastener is affixed to the flap and the other element is affixed to the base of the device.

These alternatives, however, can be relatively expensive to manufacture, particularly where the elements of hook-and-loop or snap fasteners must be fixed to the flap and base of the device. Further, these closure techniques result in the device being secured at only one point or at most several discrete points between the flap and the base of the device. This can be a particular disadvantage in test devices that require a closing force to be evenly applied between the flap and the base of the device.

Among the many such devices that are useful for detection or determination of analytes, particularly analytes of biological interest, are chromatographic assay systems, particularly chromatographic assay systems that employ opposable components to transfer fluid from one element to another. Such assay systems are becoming of increasing importance.

Among the analytes frequently assayed with such systems are:

(1) hormones, such as human chorionic gonadotropin (hCG), frequently assayed as a marker of human pregnancy, as well as luteinizing hormone (LH), thyroid stimulating hormone (TSH), and follicle stimulating hormone (FSH);

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibodies to the bacterium *Helicobacter pylori* and to human immunodeficiency virus (HIV);

(4) other proteins, such hemoglobin, frequently assayed in determinations of fecal occult blood, an early indicator of gastrointestinal disorder, such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroine, amphetamines, and marijuana; and (7) vitamins.

Such chromatographic systems are frequently used by physicians and medical technicians for rapid in-office diagnosis or therapeutic monitoring of a variety of conditions and disorders. They are also increasingly used by patients themselves for at-home monitoring of such conditions and disorders.

Among the most important of such systems are the "thin layer" systems in which a solvent moves across a thin, flat, absorbent medium. Among the most important of tests that can be performed with such thin layer systems are immunoassays, which depend on the specific interaction between an antigen or a hapten and a corresponding antibody or other specific binding partner.

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen, and if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, enzymatic activity, or another physical or chemical property.

Immunochromatographic assays fall into two principal categories: "sandwich" and "competitive," according to the nature of the antigen-antibody complex to be detected and the sequence of reactions required to produce that complex. The category of assay used is determined by the design of the device, which typically performs a reaction in a specified sequence.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

One particularly useful type of immunochromatographic test device useful for the performance of sandwich and competitive assays employs opposable components and transfers fluid from one opposable component to another during the course of the assay. Typically, such devices employ a precisely calibrated degree of pressure to transfer fluid as desired. Such devices can be constructed in a number of alternative variations.

These devices typically employ a chromatographic medium on one of the opposable components. The other of the opposable components has either a sample application zone or an applicator for applying a detection reagent, which can be a specific binding partner for the analyte or another reagent, depending on the analyte to be detected. In addition, a number of flow patterns are employed within the device.

In one flow pattern, designated "unidirectional," flow occurs along one direction of the chromatographic medium from a first end of the chromatographic medium to a second end of the chromatographic medium. This format is typically used for detection of antigens where a specific antibody exists and the antigen is suitable for assay in a sandwich format. In a second flow pattern, designated "bidirectional," a sample is applied to a first end of the chromatographic medium and traverses the chromatographic medium from its first end to its second end. At this point, the opposable elements are closed, and a detection reagent is applied to the chromatographic medium at or near the second end and traverses the chromatographic medium from the second end to the first end. This assay format is particularly suitable for serological assays in which the analyte is an antibody to a specific antigen and the detection reagent is a second antibody that binds the antibody analyte on the basis of species, class, or subclass specificity.

In a third flow pattern, generally designated "split-flow," the sample is applied to a sample application zone on the opposable element not containing the chromatographic medium, and when the opposable components are brought into operable contact, the sample is applied at a point separated from the ends of the chromatographic medium so that the flow is split, one part of the flow going to the first end and the other part going to the second end.

These differing formats add to the requirements for an improved closure.

Another aspect of these devices that places additional requirements on the closure for such test devices is that it is highly desirable that once closed for the performance of the assay, such devices remain closed and do not inadvertently open. This is particularly important in the light of the increased prevalence of diseases spread by infected blood and blood fractions, such as AIDS and hepatitis. It therefore would be highly desirable to have an improved closure device that can maintain the device in a closed position once the assay has been performed, reducing the risk when the device is disposed.

Additionally, the closure must accommodate varying degrees of pressure as is optimum for each assay format. The internal pressure may be increased if the device incorporates an additional interior component or thicker interior components such as a cotton swab.

One type of closure that has been used in such assay devices is the bevel closure, disclosed in U.S. Pat. No. 5,441,698 to Norell, incorporated herein by this reference. Although the bevel closure has proven useful, after extended use of the bevel closure in a manufactured product, it became apparent that the angle most suitable from a manufacturing standpoint conflicted with angles providing ease of use, i.e. opening and closing of the device, from the customer's perspective. The cut angle providing the most secure closure is consistently more acute than the angle easiest to close.

Thus, there is a need for a closure for use, for example, in testing devices that is relatively simple and inexpensive, and allows the devices to be opened and closed several times without destroying or substantially degrading the performance of the closure, and can apply a closing force evenly between a device flap and a base. Preferably, there is a need to both facilitate the ease of closure and to ensure a secure closure during shelf life up to the point of use and after closure during the performance of the assay to facilitate disposal of the device.

SUMMARY

The bevel closure of the present invention meets these needs by providing a closure of increased stability that ensures that testing devices incorporating the closure will stay closed during the performance of the test while providing a closure that is easier for the user to close.

One aspect of a reclosable testing device according to the present invention incorporating an improved bevel closure comprises:

(1) a base member;
(2) a cover member;
(3) a fixed member fixed to the base member, the fixed member having an undercut edge;
(4) a hinge between the base member and the cover member;
(5) a testing element fixed to at least one of the base member or the cover member; and
(6) closure means comprising an interrupted beveled edge on the cover member, the interrupted beveled edge being supplementary to the undercut edge and being adapted to be received and retained in a closed position with the undercut edge of the fixed member in a edge-to-edge engagement.

In this embodiment, the base member, cover member, and fixed member are formed of a sufficiently rigid material to minimize bowing on the closure thereby to ensure that the sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means. The beveled edge is interrupted with at least one uncut bridge region to increase the force required to separate the base member and cover member.

Preferably, the device further includes testing elements fixed to the base member and testing elements fixed to the cover member. When the testing elements are in this position, and when the beveled edge is in a closed position, typically there is a closure force for effecting transfer of a fluid between the test elements, and the beveled edge and the supplementary undercut edge are positioned and aligned from the hinge at least about opposite the test elements where the fluid transfers between the test elements. Preferably, the first and second testing elements are opposable and brought into operable contact when the cover member is closed and retained by the closure means. Typically, either the first testing elements or the second testing elements include a chromatographic medium and either the first testing elements or the second testing elements include a sample application zone. In this arrangement, the chromatographic medium and the sample application zone are not both located on either the first testing elements or the second testing elements such that the sample application zone and the chromatographic medium are brought into operable contact when the cover member is closed and retained by the closure means.

The cover member and the fixed member can extend respectively between extremities defined between ends, the beveled edge on the cover member extending from about one end of the cover member to about the opposite end of the cover member, and the supplementary undercut edge extending from about one end of the fixed member to about the opposite end of the fixed member.

The device can include an extension portion of the cover member extending beyond the beveled edge, the extension portion covering a line of closure formed by the beveled edge and the undercut edge when the cover member and the fixed member are closed.

The device can include at least two bridges or uncut regions. When there are at least two bridges, the bridges can be located in a region that is substantially less than the entire contact area between the cover member and the fixed member. Alternatively, the bridges can be located in a region that spans substantially the entire contact area between the cover member and the fixed member.

The angle of the bevel is typically between about 5 degrees to about 30 degrees from the vertical, preferably between about 6 degrees to about 15 degrees from the vertical, and most preferably from about 8 degrees to about 10 degrees from the vertical.

Another embodiment of a reclosable testing device according to the present invention comprises:

(1) a base member;
(2) a cover member;
(3) fixed members fixed to the base member, each fixed member having an undercut edge;
(4) a hinge between the base member and the cover member;
(5) a testing element fixed to at least one of the base member or the cover member; and
(6) closure means comprising interrupted beveled edges on the cover member, the beveled edges being supplementary to the undercut edges and being adapted to be received and retained in a closed position with the undercut edges of the fixed member in an edge-to-edge engagement.

In this embodiment, the base member, cover member, and fixed member are formed of a sufficiently rigid material to minimize bowing on the closure thereby to ensure that the sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means. The beveled edges are interrupted with at least one uncut bridge region to increase the force required to separate the base member and cover member.

Typically, the device includes a testing element fixed to the base member and a testing element fixed to the cover member, whereby when the beveled edge is in a closed position there is a closure for effecting transfer of a fluid between the testing elements. Typically, at least one portion of the interrupted beveled edge and one portion of the undercut edge are positioned and aligned from the hinge at least about opposite the test elements where the fluid transfers between the test elements, and another portion of the interrupted beveled edge and another portion of the undercut edge are located at a position removed from the element where the fluid transfers between the test elements.

Typically, in this embodiment, the fixed member and the cover member respectively include corners remote from the hinge and the undercut edges and the beveled edges respectively are located at the corners, and not between the respective corners.

Typically, in this embodiment, the base member includes opposite ends directed transversely from the hinge, and further includes a fixed member located at each respective end and the beveled edges are located respectively at the opposite ends, thereby to constitute closures on at least two sides of the device.

Alternatively, the base member includes an adjacent end directed transversely from the hinge and a side opposite the hinge and the beveled edge and the undercut edge are located respectively at the adjacent end and the opposite end, thereby to constitute closures on at least two sides of the device in an alternative arrangement.

Another embodiment of a reclosable testing device according to the present invention comprises:

(1) a base member;
(2) a cover member having an interrupted beveled edge;
(3) a fixed member fixed to the base member, the fixed member having an undercut edge being supplementary to the beveled edge;
(4) a hinge between the base member and the cover member, wherein closure of the cover member on the base member effects engagement of the beveled edge with the undercut edge of the fixed member, the interrupted beveled edge being adapted to be received and retained in a closed position in an edge-to-edge engagement with the undercut edge of the fixed member; and
(5) a testing element fixed to the base member and a testing element fixed to the cover member, the members being in operable contact when the cover member and the base member are closed.

In this embodiment, the base member, the cover member, and the fixed member are formed of a sufficiently rigid material to minimize bowing on the closure thereby to ensure that a sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means. In this embodiment, the beveled edge is interrupted with at least one uncut bridge region to increase the force required to separate the base member and cover member.

In this embodiment, typically, the cover member and fixed member are extended respectively between extremities defined between ends, the beveled edge of the cover member extending from about one edge of the cover member to about the opposite end of the cover member, and the supplementary undercut edge extending from about one end of the fixed member to about the opposite end of the fixed member.

The interrupted beveled edge and the supplementary undercut edge can be positioned and aligned from the hinge at least about opposite the test elements.

A device according to this embodiment can further include an extension portion of the cover member extending beyond the beveled edge, the extension portion covering a line of closure formed by the interrupted beveled edge and the undercut edge when the cover member and the fixed member are closed.

Another embodiment of a reclosable testing device according to the present invention comprises:

(1) a base member;
(2) a cover member having interrupted beveled edges;
(3) fixed members fixed to the base member, the fixed members having undercut edges, the undercut edges being supplementary to the interrupted beveled edges such that in a closed position of cover member and base member the interrupted beveled edges and the undercut edges are in edge-to-edge alignment;
(4) a hinge between the base member and the cover member; and
(5) a testing element fixed to the base member and a testing element fixed to the cover member, the testing elements being in operable contact when the cover member and the base member are closed.

In this embodiment, the base member, cover member, and fixed member are formed of a sufficiently rigid material to minimize bowing on the closure, thereby to ensure that a sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means. The beveled edge is interrupted with at least one uncut bridge region to increase the force required to separate the base member and cover member.

Typically, in this embodiment, the base member includes opposite ends directed transversely from the hinge, and includes fixed members located at each respective end and the interrupted beveled edges and undercut edges are located respectively at the opposite ends, and further includes an elongated chromatographic medium with at least one of the elements for fluid to traverse the chromatographic medium in a defined flow path. In one alternative, the defined flow path is from the first end of the chromatographic medium to a second end of the chromatographic medium. In another alternative, the defined flow path is from a point removed from both a first end and a second end of the chromatographic medium toward both the first end and the second end of the chromatographic medium.

In this embodiment, the base member can include an adjacent end located transversely from the hinge, and including a side opposite the hinge. The interrupted beveled edges and the undercut edges can be located respectively at the adjacent end and the opposite side. The device can include an elongated chromatographic medium with at least one of the test elements for fluid to traverse the chromatographic medium in a defined flow path, as defined above.

Typically, in this embodiment of the device, when the interrupted beveled edge is in a closed position, a closure force is applied between the cover member and the fixed member, and at least one portion of the interrupted beveled edge and one portion of the undercut edge are positioned and aligned from the hinge at least about opposite the test elements and another portion of the interrupted beveled edge and another portion of the undercut edge are located at a position removed from the elements.

In this embodiment, the testing device can include a window located in at least one of the base member and cover member, the window being aligned along the length of the chromatographic medium such that a test indication on the chromatographic medium is visible through the window when the base member and the cover member are in a closed position.

The fixed members and the cover member can respectively include corners remote from the hinge, and the undercut edges and the interrupted beveled edges can be located at the corners and not between the respective corners.

Another embodiment-of an reclosable testing device according to the present invention comprises:

(1) a base member;

(2) a cover member;

(3) a fixed member fixed to the base member, the fixed member having an undercut edge;

(4) a hinge between the base member and the cover member;

(5) a testing element fixed to the base member and a testing element fixed to the cover member, at least one of the testing elements including an elongated chromatographic medium, and wherein one of the testing elements is arranged for receiving fluid and for transferring fluid to the testing element having the chromatographic medium, whereby the fluid is arranged to traverse along the chromatographic medium along a defined flow path; and (6) closure means comprising an interrupted beveled edge on the cover member, the beveled edge being supplementary to the undercut edge and being adapted to be received and retained in a closed position with the undercut edge of the fixed member in an edge-to-edge engagement.

In this embodiment, the base member, cover member, and fixed member are formed of a sufficiently rigid material to minimize bowing on the closure, and thereby to ensure that, together with the hinge between the base member and the cover member, and with the closure means, the closure force is substantially equally distributed along the length of the closure means whereby when the interrupted beveled edge is in the closed position, a closure force is distributed substantially uniformly between the cover member and the fixed member such that the fluid is effectively transferred between the testing elements and is enabled to effectively traverse the chromatographic medium. The beveled edge is interrupted with at least one uncut bridge region to increase the force required to separate the base member and cover member.

In this embodiment, the base member and the cover member are typically formed from the same board material element and the hinge typically includes at least one crease formed in the board material, the board material having a thickness of about 0.024 inches.

In this embodiment, typically the base member and the cover member are planar elements formed from the same material element having a thickness and the hinge is formed along a crease line in the material and the test elements are located in adjacency on the covered member and the base member and the fixed member is mounted on a portion of the base member, such that in a position of closure, the cover member overlies the position of the base member not occupied by the fixed member, and the cover member and fixed member have edges in abutment, and wherein inward force is applied by the cover member and the base member on the test element substantially uniformly when the edge of the fixed member and the edge of the cover member are in edge-to-edge engagement.

Another embodiment of a reclosable testing device according to the present invention comprises:

(1) a base member;

(2) a cover member;

(3) fixed members fixed to the base member, each fixed member having an undercut edge;

(4) a hinge between the base member and the cover member;

(5) a testing element fixed to the base member and a testing element fixed to the cover member, at least one of the testing elements including an elongated chromatographic medium, and wherein one of the testing elements is arranged for receiving fluid and for transferring the fluid to the testing element having the chromatographic medium, whereby the fluid is arranged to traverse along the chromatographic medium along a defined flow path; and (6) closure means comprising interrupted beveled edges on the cover member, the interrupted beveled edge being supplementary to the undercut edges and being adapted to be received and retained in a closed position with the undercut edges of the fixed members in an edge-to-edge engagement.

In this embodiment, the base member, the cover member, and the fixed member are formed of a sufficiently rigid material to minimize bowing on the closure, thereby to ensure that, together with the hinge between the base member and the cover member, and with the closure means, the closure force is substantially equally distributed along the length of the closure means whereby when the beveled edge is in the closed position, a closure force is distributed substantially uniformly between the cover member and the fixed members such that the fluid is effectively transferred between the testing elements and is enabled to effectively traverse the chromatographic medium. The beveled edge is interrupted with at least one uncut bridge region to increase the force required to separate the base member and cover member.

In this embodiment, the base member and the cover member can be planar elements formed from the same material element having a thickness, the hinge can be formed along a crease line in the material and the test elements can be located in adjacency on the covered member and the base member and the fixed members are mounted on a position of the base member, such that in a position of closure the covered portion overlies the portion of the base member not occupied by the fixed members. The cover member and fixed members have edges in abutment, and inward force applied by the cover member and the base member on the test elements toward each other is effected uniformly when the edge of the fixed member and the edge of the cover member are in the edge-to-edge engagement.

Another embodiment of a reclosable testing device according to the present invention comprises:

(1) a base member;
(2) a cover member having an interrupted beveled edge, the interrupted beveled edge including an exposed line of engagement;
(3) a fixed member fixed to the base member, the fixed member having an undercut edge being supplementary to the interrupted beveled edge and including an exposed line of engagement;
(4) a hinge between the base member and the cover member; closure of the cover member on the base member effecting engagement of the interrupted beveled edge with the undercut edge, the interrupted beveled edge being adapted to be received and retained in a closed position in an edge-to-edge engagement with the undercut edge of the fixed member. In this embodiment, the base member, the cover member and fixed member are formed of a sufficiently rigid material to minimize bowing on the closure thereby to ensure that its sample for testing and the testing element come into operable contact for effecting a test, and that a force is distributed substantially evenly over the cover member and thereby further ensuring that, together with the hinge between the base member and the cover member, and with the closure means, the closure force is substantially equally distributed along the length of the closure means. The beveled edge is interrupted with at least one uncut bridge region to increase the force required to separate the base member and cover member.

Typically, in this embodiment, the base member and the cover member are planar elements formed from a same material element having a thickness and the hinge is formed along the crease line in the material, and the test elements are located in adjacency on the cover member and the base member and the fixed member is mounted on a portion of the base member, such that in a position of closure, the covered portion overlies the portion of the base member not occupied by the fixed member, and the cover member and fixed member have edges in abutment, and wherein an inward force applied by the cover member and the base member on the test elements toward each other is effected uniformly when the edges of the fixed member and the edges of the cover member are in the edge-to-edge engagement.

Another embodiment of a reclosable testing device according to the present invention comprises:

(1) a base member;
(2) a cover member having interrupted beveled edges, the interrupted beveled edges including exposed lines of engagement;
(3) fixed members fixed to the base member, the fixed members having undercut edges, the undercut edges being supplementary to the interrupted beveled edges and including exposed lines of engagement;
(4) a hinge between the base member and the cover member; and
(5) a testing element fixed to the base member and a testing element fixed to the cover member, at least one of the testing elements being arranged for receiving fluid and for transferring fluid to the other testing element; closure of the cover member on the base member effecting engagement of the interrupted beveled edges to be received and retained in edge-to-edge contact in the closed position with the undercut edges of the fixed members and the exposed lines of engagement of the beveled edges and the undercut edges respectively being substantially flush to the fixed members and the cover member.

In this embodiment, the base member, cover member, and fixed member are formed of a sufficiently rigid material to minimize bowing on the closure thereby to ensure that a sample for testing and the testing element come into operable contact for effecting a test, and that a force is distributed substantially evenly over the cover member and thereby further ensuring that, together with the hinge between the base member and the cover member, and with the closure means, the closure force is substantially equally distributed along the length of the closure means. The beveled edge is interrupted with at least one uncut bridge region to increase the force required to separate the base member and cover member.

Typically, in this embodiment, the base member and the cover member are planar elements formed from a same material element having a thickness and the hinge is formed along a crease line in the material and the test elements are located in adjacency on the cover member and the base member and the fixed members are mounted on a portion of the base member, such that in a position of closure, the covered portion overlies the portion of the base member not occupied by the fixed members. The cover members and fixed members have edges in abutment. An inward force applied by the cover member and the base member on the test elements toward each other is affected uniformly when the edge of the fixed members and the edge of the cover member are in the edge-to-edge engagement.

BRIEF DESCRIPTION OF THE DRAWINGS

These and other features, aspects, and advantages of the present invention will become better understood with reference to the following description, appended claims, and accompanying drawings where:

FIG. 13 is a view of another form of a testing device utilizing the interrupted bevel closure in accordance with the present invention;

FIG. 14 is a view of the opposite side of the device of FIG. 13;

FIG. 15 is a perspective view of another form of a testing device in accordance with the present invention employing an interrupted bevel closure;

FIG. 16 is a top view of another device in accordance with the present invention employing an interrupted bevel closure;

FIG. 17 is a side view of a device in accordance with the present invention, having a covered closure employing an interrupted bevel closure;

FIG. 18A illustrates a alternative form of a closure in accordance with the present invention employing an interrupted bevel closure, depicted in cross-sectional view through a portion of the bevel closure that does not have uncut regions forming bridges;

FIG. 18B depicts a cross-sectional view through the interrupted bevel closure of FIG. 18A in a portion that has uncut regions forming bridges;

FIG. 18C illustrates another alternative form of a closure in accordance with the present invention employing an interrupted bevel closure, depicted in cross-sectional view through a portion of the bevel closure that does not have uncut regions forming bridges;

FIG. 19 is a perspective view of another device in accordance with the present invention employing an interrupted bevel closure.

DESCRIPTION

I. THE BEVEL CLOSURE

Figure 1:
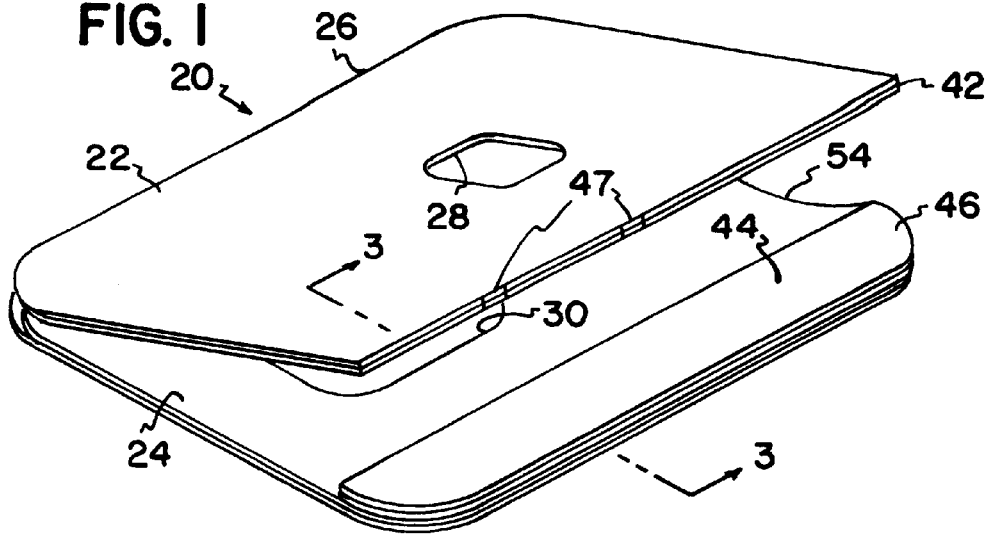
FIG. 1 is a perspective view of a testing device incorporating a closure employing an interrupted beveled edge in accordance with the present invention.

The bevel closure of the testing device according to the present invention is modified from the bevel closure in U.S. Pat. No. 5,441,698 to Norell, incorporated herein by this reference, by being interrupted by one or more uncut portions or bridges. As in U.S. Pat. No. 5,441,698 to Norell, the bevel closure is between two members of a testing device: a cover member and a fixed member. The beveled edge is formed between a cover member and a fixed member of an assay device as shown below. The bevel angle and the undercut angle are equal. Typically, the bevel angle is between about 5° to about 30° from the vertical. Preferably, the angle is from about 6° to about 15° from the vertical. More preferably, the angle is from about 8° to about 10° from the vertical, depending upon the type of blade selected.

As indicated above, the bevel is interrupted leaving one or more uncut region or regions. There can be one uncut region or bridge; alternatively, there can be two or more uncut regions or bridges. If there is more than one uncut region or bridge, the bridges can be located in a localized region that spans substantially less than the entire contact area between the cover member and the fixed member. Alternatively, the bridges can span substantially the entire contact area between the cover area and the fixed member.

As detailed below, these bridges or uncut regions are introduced by notching or nicking the rotary blade used in manufacturing (FIGS. 9–12). The rotary blade used in manufacturing previously had a smooth edge that made a continuous cut. The blade is modified to effect interruptions in the cut, such that a perforated cut is made on the material. Modification of the blade involves notching, or nicking, the edge at various points along the circumference. These nicks can be any combination of various shapes, depths, and/or angles with the desired spacing. When the blade edge penetrates the surface to be cut, the uncut portion of the surface results in points corresponding to each nick in the blade. This uncut portion or bridge takes the shape of the nick in the blade. This configuration of nick shape, depth, angle, and spacing, combined with a selected angle at which the blade makes contact as described in U.S. Pat. No. 5,441,698 to Norell, determines the ease of opening and closing of the device. The shape, size and spacing of the bridges in the interrupted bevel cut determines the ease in opening and closing of the device. Among the variables one of ordinary skill in the art would consider in selecting the arrangement of bridges are the materials used in the test device and the thickness of elements within the test device, such as a chromatographic medium or other fluid-carrying elements as described below. A device containing elements with greater thickness would exert greater outward pressure against the closure.

In this instance, the use of a greater number of bridges is preferable. Similarly, the use of additional interior components such as cotton swabs as part of the device will also dictate the use of blade configurations that would provide a more secure closure. In general, the smaller the angle, i.e., the closer the angle is to the vertical, the easier the closure would be to open. However, this is compensated by the use of the bridges or uncut regions.

II. TESTING DEVICES

One aspect of the present invention comprises reclosable testing devices, particularly chromatographic assay devices. These devices are particularly useful for the assay of analytes in biological samples. Although these devices can be constructed according to many patterns, one particularly useful device according to the present invention is suitable for the direct application of biological samples, without preliminary extraction steps, and is constructed so as to minimize interference with assay results caused by particulates or colored samples.

Typically, a reclosable testing device according to the present invention has at least two opposable components that function as a part of the assay device. These opposable components are typically substantially planar. Typically, the testing device is a chromatographic assay device that performs immunochromatography. In this alternative, one of the substantially planar components has in its surface a chromatographic medium. When there are two opposable components, one of the opposable components is designated the first opposable component and the other is designated the second opposable component. Typically, the first opposable component is the component with the chromatographic medium. This distinction is arbitrary and for convenience in description; the role of each of the opposable components is determined by the element or elements located on it.

As recited below, the housing of the device including the base member, the cover member, the fixed member and the closure means cooperate in providing means for opposing the opposable components, also referred to as bringing them into operable contact, and applying pressure thereto. Typically, this is performed by direct manual closure. The pressure applied is sufficient to transfer fluid from one opposable component to another opposable component in a direction substantially normal to opposable components in a sequence determined by the construction of the assay device and particularly by the construction of the base member, the cover member, the fixed member fixed to the base member, and the closure means. The end result is that the sample is applied to the chromatographic medium for detection or determination of the analyte thereon. The pressure also drives the fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. One function of the bevel closure is to maintain this pressure when the device is closed so that the device does not open during the performance of the assay. Typically, the assay device is read through a window in the device while the device remains closed. Therefore, there is no need to reopen the device to read the result, and, in order to facilitate handling and disposal of the device, it is preferable for the device to remain closed once the opposable components have been brought into opposition or operable contact.

The degree of pressure employed in a device can be regulated so that it is optimum for the characteristics of the chromatographic medium analyte and label. As indicated above, the bevel closure is involved in regulating the pressure within the device.

Assay methods using a device according to the present invention can give a qualitative, semi-quantitative, or quantitative indication of analyte presence or concentration, depending upon the concentration of the labeled specific binding partner at the detection zone and the size of the detection zone, as well as the detection method used. In general, in the specification, the term "detect" is used to refer to a qualitative indication of the presence or absence of an analyte, while the term "determine" is used to refer to either a semi-quantitative or a quantitative determination of the concentration of the analyte. The term "observe" is typically used to refer to a visual observation leading to a qualitative or semi-quantitative determination or detection of analyte presence or concentration, while the term "measure" is typically used to refer to an instrumental measurement that yields a quantitative determination of analyte concentration. Such a measurement is typically by spectroscopy, although other methods can be used.

A. Elements Common to The Device According to the Present Invention

A number of elements are common to reclosable testing devices according to the present invention and are discussed here for convenience.

1. The Chromatographic Medium

The chromatographic medium is a strip, typically, the strip is substantially planar, although this is not required for all embodiments. Departures from substantial planarity of the chromatographic medium affect the degree of pressure required within the device and thus the design of the bevel closure. It is typically rectangular, having first and second ends and first and second surfaces. Except in the case of split flow, described below, the term "first end" refers to the end at or near which liquid is applied to the chromatographic medium and the term "second end" applies to the opposite end of the chromatographic medium. In split-flow devices, liquid is applied at or near the center of the chromatographic medium and flows in both directions. When liquid is applied at a first end of the chromatographic medium it can be, but is not necessarily, a sample or a treated sample, and can contain a resolubilized labeled specific binding partner for the analyte. Alternatively, as indicated below, the chromatographic medium can contain a zone of resolubilizable label specific binding partner for the analyte in a zone referred to as the "conjugate zone."

The chromatographic medium is composed of material suitable as a medium for thin-layer chromatography of analyte and analyte-antibody conjugates, such as nitrocellulose, cellulose acetate, nylon, rayon, cellulose, paper, or silica. Preferably, the chromatographic medium is nitrocellulose.

The chromatographic medium can be pretreated or modified as needed. Typically, the chromatographic medium is translucent, so that the colored zones appearing on it can be viewed from either side, such as through an aperture. As detailed below, the reclosable testing device according to the present invention typically includes an aperture.

2. Absorbers

In a number of devices according to the present invention, absorbers can be brought into operable contact with at least one end of the chromatographic medium. The absorbers can be made of any bibulous material that will hold liquid sufficiently so that liquid can be drawn through the chromatographic medium and accumulated in the absorber. Typical materials for the absorber include, but are not limited to, cellulose and filter paper. The size and shape of the absorber can be chosen according to the volume of fluid used in the assay.

3. Sample Application Zones

In devices according to the present invention, sample application zones are typically found. These elements are designed to receive a sample to be assayed. These elements can contain reagents for treatment of the sample or for filtration of the sample, such as for removing particulates. Depending on the arrangement of the device, they can be found on either the first opposable component or the second opposable component. The degree of pressure exerted by the bevel closure according to the present invention can be varied according to the arrangement of the sample application zone. The sample application zones are typically prepared of hydrophilic media that pass liquids without substantially absorbing them. Such materials are well known in the art. In some cases, these elements can have incorporated therein a component in dry form that can be resolubilized by addition of a liquid to the element, typically an aqueous liquid such as a sample. The terms "resolubilized," "resolubilizable," and similar terminology are used herein generally to refer to the state of such components.

4. Applicators

In some embodiments of the reclosable testing devices according to the present invention, an applicator is located on either the first or second opposable component or both the first and second opposable components. The applicator is for applying fluid to the chromatographic medium during the performance of the assay. The applicator can contain a component in resolubilizable form, such as a label specific binding partner for the analyte. These elements are also typically prepared of hydrophilic media that pass liquids without substantially absorbing them as described above for sample application zones.

5. Conductors

In some arrangements of reclosable testing devices according to the present invention, one or more conductors are in operable contact with the chromatographic medium or other elements of the testing device. As indicated above, these elements are typically prepared of hydrophilic media that pass liquids without substantially absorbing them.

6. Opposable Components

Any of the embodiments of the assay device according to the present invention comprise two opposable components incorporated in the testing device. Typically, one of the components is a cover member and the other member is a fixed member fixed to a base member. The bodies of the opposable components are preferably made of a laminated cellulose-based material that is sufficiently impervious to moisture to contained liquids involved in the performance of the assay carried out by the device. Examples of such materials include paperboard and fiberboard. A preferable material for the opposable components is solid bleached sulfite (SBS) paperboard, approximately 0.024 inch thick. Alternatively, the bodies of the opposable components can be made of plastic that is impervious to moisture. A suitable plastic is polycarbonate plastic such as Lexan™.

The opposable components are typically joined by a hinge, as discussed below.

7. Labeled Components

For assay devices intended to perform a sandwich immunoassay, the labeled component is typically a labeled specific binding partner to the analyte. The labeled component is typically mobile, in that it can migrate through the chromatographic medium, whether free or bound to an analyte. The label is preferably a visually detectable label, such as a colloidal label. The colloidal label can either be a colloidal metal label or a non-metallic colloidal label.

A preferred non-metallic colloidal label is colloidal carbon. Colloidal carbon labels for labeling of specific binding partners are described, for example, in U.S. Pat. No. 5,529,901 to Van Doorn et al., incorporated by this reference.

If a colloidal metal label is used, preferably, the colloidal metal label is gold, silver, bronze, iron, or tin; most preferably, it is gold. The preparation of gold labeled-antibodies and antigens is described in J. DeMay, "The Preparation and Use of Gold Probes", in *Immunocytochemistry: Modern Methods and Applications* (J. M. Polak & S. VanNoorden, eds., Wright, Bristol, England, 1986), ch. 8, pp. 115–145, incorporated herein by this reference. Antibodies labeled with colloidal gold are commercially available, such as from Sigma Chemical Company, St. Louis, Mo.

Alternatively, still other colloidal labels, such as a dye-silica label, can also be used. In a less preferred alternative, the visually detectable label can be a colored latex label. It is also possible to use other labels, such as a radioactive label, a fluorescent label, or an enzyme label.

The location of the labeled component varies with the assay format and can affect the details of construction of the interrupted bevel closure.

B. Details of Testing Devices According to the Present Invention

Figure 2:
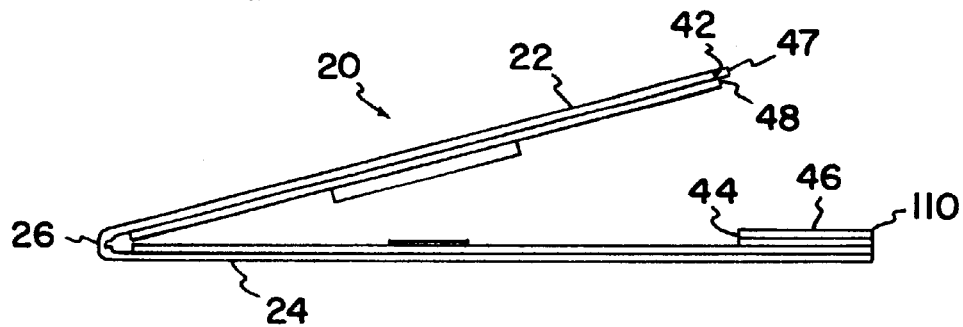
FIG. 2 is a side view of the device of FIG. 1.
Figure 3:
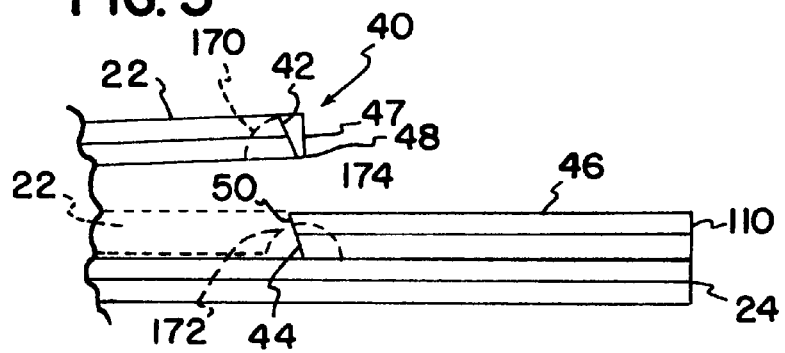
FIG. 3 is a section view taken along line 3—3 of FIG. 1.

With reference to FIGS. 1, 2, and 3, a first embodiment of a testing device according to the present invention 20 includes a first planar member in the form of a front panel 22 and a back panel 24. The front panel 22 and the back panel 24 are joined by a hinge 26. Typically, the front panel 22 includes a window 28 for observing test results and the back panel 24 includes a well 30 adapted to receive testing elements and reagents as described more fully below with respect to FIG. 4.

As shown in FIG. 1–3, the testing device 20 includes a closure 40 in accordance with the present invention. The closure 40 includes an interrupted beveled edge 42 formed at an edge of the front panel 22 opposite to that of the hinge 26 and an undercut edge 44 formed on a closure portion or planar fixed member 46 that is fixed to the back panel 24. The interrupted beveled edge 42 includes one or more uncut regions or bridges 47; in the diagram of FIGS. 1–3; two bridges are shown, but as indicated above, the number can vary.

To close the testing device 20 using the closure 40, the front panel 22 is rotated about the hinge 26 so that the cover or panel 22 and base or back panel 24 are brought together with a protruding lip or corner 48 of the interrupted beveled edge 42 brought against the upper surface of the fixed member 46. The front and back panels 22 and 24 are urged together, slightly flexing the testing device 20 and in particular, the hinge 26, allowing the protruding corner 48 to be displaced between an overhanging corner 50 of the undercut edge 44. With the entire length of the interrupted beveled edge 42 thus captured by the undercut edge 44 as illustrated by the phantom outline in FIG. 3, the testing device 20 is closed with the front panel 22 in an opposed orientation with respect to the back panel 24. It is seen that the hinge 26 acts as a means for positioning the front and back panels 22 and 24 such that the interrupted beveled edge 42 is captured, engaged, or retained by the undercut edge 44.

Conversely, to open the testing device 20, the front and back panels 22 and 24 are urged apart as for example, by holding the fixed member 46 and the back panel 24 between the user's fingers and urging the front panel 22 away from the back panel 24. An outer edge of the front panel 22 can be conveniently accessed via a notch 54 formed in the back panel 24. With opening force applied by the user, the testing device 20 and in particular the hinge 26 again slightly flex, releasing the interrupted beveled edge 42 from the undercut edge 44 and thereby allowing the front panel 22 to be opened with respect to the back panel 24. The bridges 47 increase the force required to open the front panel 22 with respect to the back panel 24 for a particular angle of the bevel.

Figure 4:
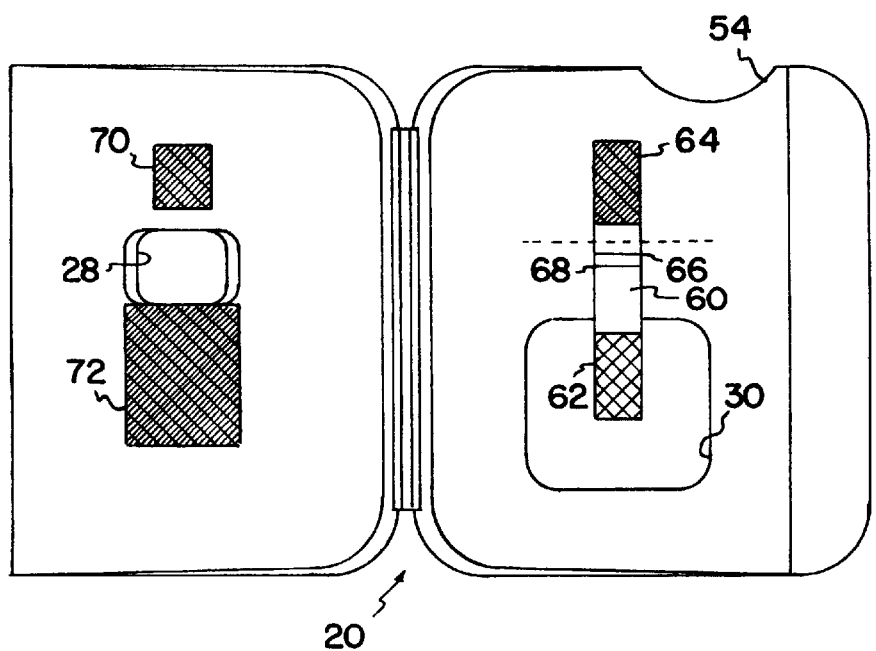
FIG. 4 is a view of the device of FIG. 1 opened up to reveal testing structures.

With reference to FIG. 4, the testing device 20 can include testing elements for the analysis of a sample, such as by an immunoassay. The testing elements can include, with respect to the particular embodiment of FIG. 4, a chromatographic medium 60, a sample application zone 62 and a conductor 64 on the inside of the back panel 24. The chromatographic medium 60 can also include first and second lines 66 and 68 of immobilized components useful for demonstrating the performance of the testing device 20 and detecting the presence of an analyte in a sample.

Typically, one of 66 and 68 is a detection zone that typically contains an immobilized specific binding partner for the analyte. When the analyte is an antigen, this immobilized specific binding partner is typically an antibody for the antigen. When the analyte is an antibody, in one alternative, the specific binding partner in the detection zone is typically an immobilized antigen for which the antibody is specific. The other of 66 and 68 is typically a control zone which binds a labeled specific binding partner for the analyte or another labeled specific binding partner that binds a specific binding partner immobilized at the control zone.

In the alternative shown in FIG. 4, the device performs a bidirectional immunoassay. In this alternative, the inside of the front panel 22 includes an applicator 70, including a labeled specific binding partner for the analyte in resolubilizable form, and an absorber 72. The first and second lines of immobilized components 66 and 68 are aligned to be visible through the window 28. As so configured, the testing device 20 forms an immunochemical testing device for the detection of, for example, antibody to the bacterium *Helicobacter pylori* as described in U.S. patent application Ser. No. 07/888,831, filed May 27, 1992, in the name of Howard M. Chandler, entitled "Assay Device" and which is assigned to the same assignee as the present invention, all of which is incorporated herein by this reference. This is an example of a bidirectional immunoassay format. Devices such as those shown in FIGS. 1–3 can also be used for unidirectional or split-flow formats. In a unidirectional format, flow occurs along the chromatographic medium in one direction, from the first end of the cluromatographic medium to the second end of the chromatographic medium. Typically, in a unidirectional assay, a sandwich format is used and detection occurs by formation of a ternary "sandwich" complex at the detection zone, consisting of an immobilized unlabeled specific binding partner for the analyte, the analyte, and a mobile labeled specific binding partner for the analyte.

In another alternative, the split-flow format, fluid is applied to the chromatographic medium at a point removed from both the first and second ends and flow proceeds in two directions at once to both the first and second ends. This is particularly useful for sandwich immunoassays, although it can be used for other types of assays as well.

The arrangement of testing elements varies with the assay format and would be apparent to one of ordinary skill in the art with the choice of assay format.

Preferably, the testing device 20 is made of paperboard or fiberboard, and is preferably solid bleached sulfite (SBS) paperboard approximately 0.024 inch thick. However, this thickness can be varied depending upon the assay format chosen, the reagents used, the label used, the volumes of sample and labeled specific binding partner to be accommodated, and other factors known to one of ordinary skill in the art.

Figure 5:
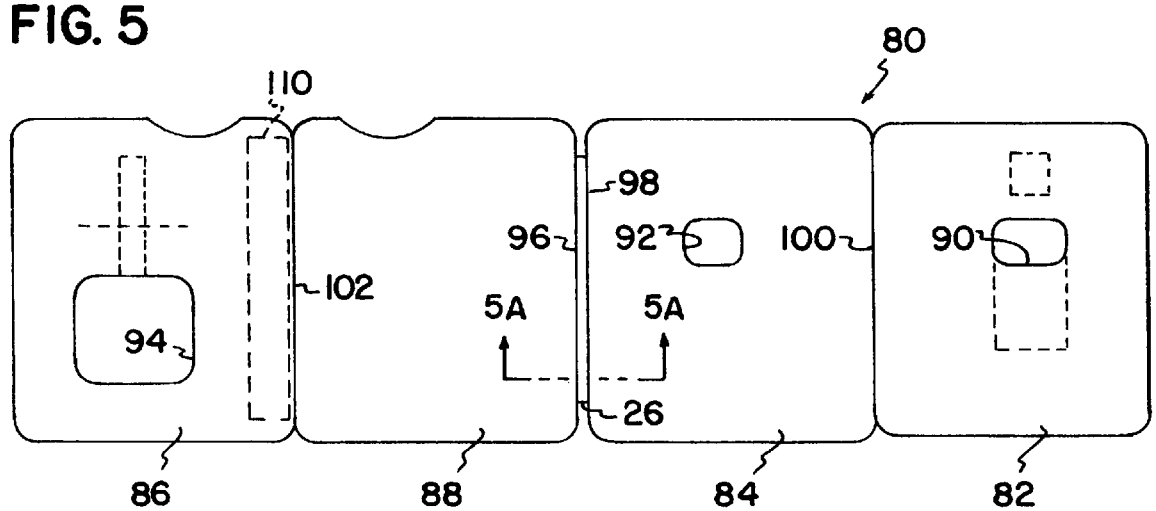
FIG. 5 is a blank from which the device of FIG. 1 can be formed.

The material can be cut to form a blank 80 (FIG. 5). The blank 80 includes a first front panel portion 82 and a second front panel portion 84, as well as a first back panel portion 86 and a second back panel portion 88. The window 28 is formed by first and second openings 90 and 92 formed in the first and second front panel portions 82 and 84. Similarly, the well 30 is formed by a third opening 94 formed in the first back panel portion 86. Two parallel-two-point crease rules 96 and 98 (FIG. 5A) are approximately two points apart and aid in forming the hinge 26, an overall distance 97 from the outside edges of the crease rules 96 and 98 accordingly being about six points. As an alternative, a six point crease rule 99 (FIG. 5B) can replace the two crease rules of FIG. 5A. Other crease rules can be used according to the needs of the particular hinge that is to be formed. This can vary according to the volume of the sample, the volume of other reagents to be applied, the thickness of the front and back panels 22 and 24, and other factors.

The first cut or score line 100 is cut into the surface of the blank 80 between the first and second front panel portions 82 and 84 to aid in forming a sharp fold line between the first and second front panel portions 82 and 84. A similar second cut or score line 102 is cut into the surface of the blank 80 between the first and second back panel portions 86 and 88.

The blank 80, with the openings 90, 92 and 94, and the score lines 100 and 102, is preferably die-cut and formed all in a conventional fashion. With the blank 80 formed, the first and second panel portions 82 and 84 are folded along the first score line 100, bringing the first and second front panel portions 82 and 84 together. A piece of clear plastic window material or other clear window material can be disposed between the first and second front panel portions 82 and 84, thus providing a clear plastic material (not shown in FIG. 5) within the window 28. Preferably, the first and second front panel portions 82 and 84 are glued together. Suitable adhesives are well-known in the art and need not be described further here. Similarly, the first and second back panel portions 86 and 88 are folded along the second score line 102 and are glued together. The various testing elements such as those described with respect to FIG. 4 are applied to the testing device. An adhesive 110, shown in cross-section in FIG. 3 and shown in outline form in FIG. 5, is applied to the first back panel 86 proximate to the position where the closure is to be formed (as is described below). The blank 80 is then folded along the hinge 26 and the front and back panels 22 and 24 are pressed together, particularly along the adhesive 110, placing the applicable test elements in opposition.

To form the closure 40, an angled cut is made in the front panel 22. In the embodiment disclosed herein, a modified bevel cutter 120 as illustrated in FIGS. 6–12 is used to form such a cut. The bevel cutter 120 includes a base 122 and a vertical back member 124. The base 122 includes an adjustable edge guide or straight edge 126, and a handle 128. Mounted to the vertical back member 124 are two linear rails 130 and 132 which in turn carry and support a cutting head 136. The cutting head 136 includes a linear bearing portion 138 that is supported and guided by the linear rails 130 and 132. The linear bearing portion 138 in turn supports the blade assembly 140. A vertical adjustment knob and screw 142 allows vertical adjustment of the blade assembly 140 with respect to the linear bearing portion 138. The blade assembly 140 carries a rotary blade 144 within a rotary blade holder 146. In this invention, the rotary blade 144 is modified by cuts, notches, or nicks at various points along the circumference. These nicks can be any combination of various shapes, depths, and special angles with desired spacing. When the edge of the rotary blade 144 penetrates the surface to be cut, an uncut portion of the surface results with points corresponding to each nick in the blade 144. This uncut portion or bridge takes the shape of the nick in the blade. This combination of nick shape, depth, angle and spacing together with the angle at which the blade 144 makes contact determines the ease of opening and closing of the device 20.

Figure 9A:
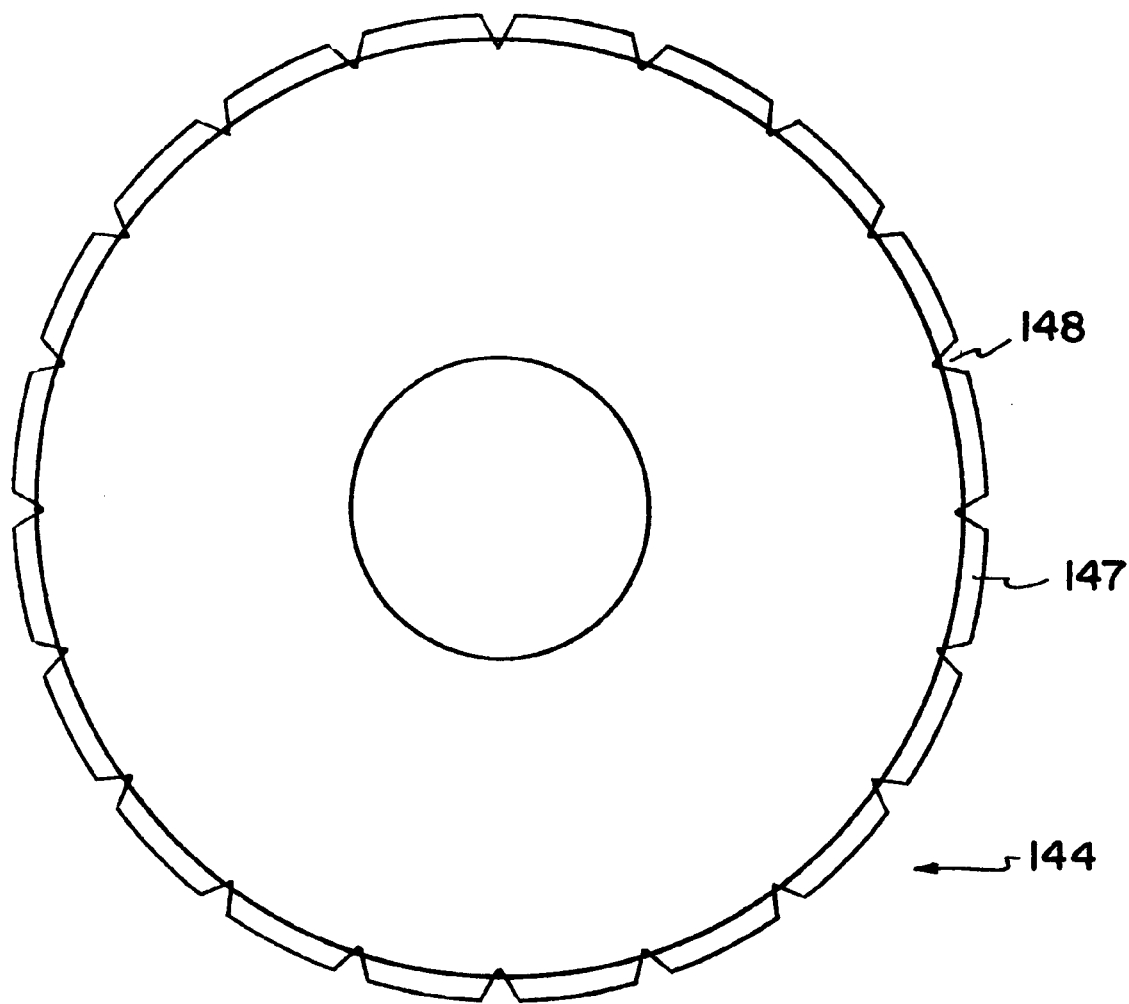
FIG. 9A is a plan view of a first version of a modified rotary blade for use in a cutter for forming the closure of the device of FIG. 1, with V-shaped interruptions or nicks.
Figure 9B:
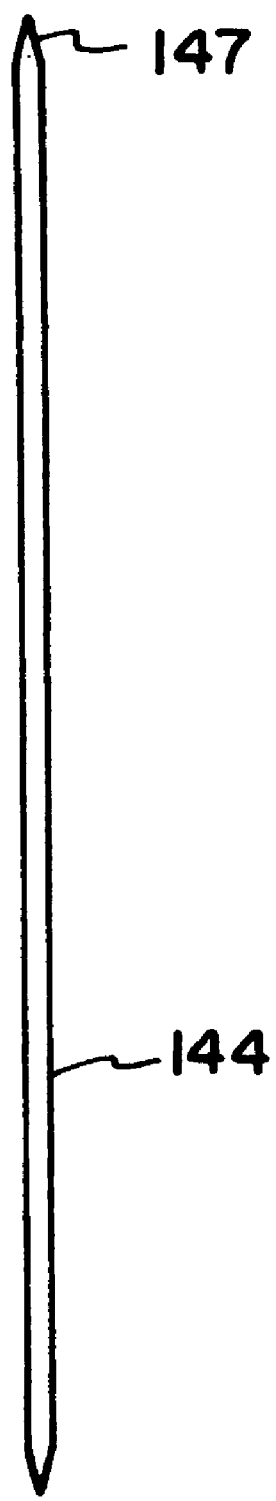
FIG. 9B is an end or profile view of the modified rotary blade of FIG. 9A.
Figure 10A:
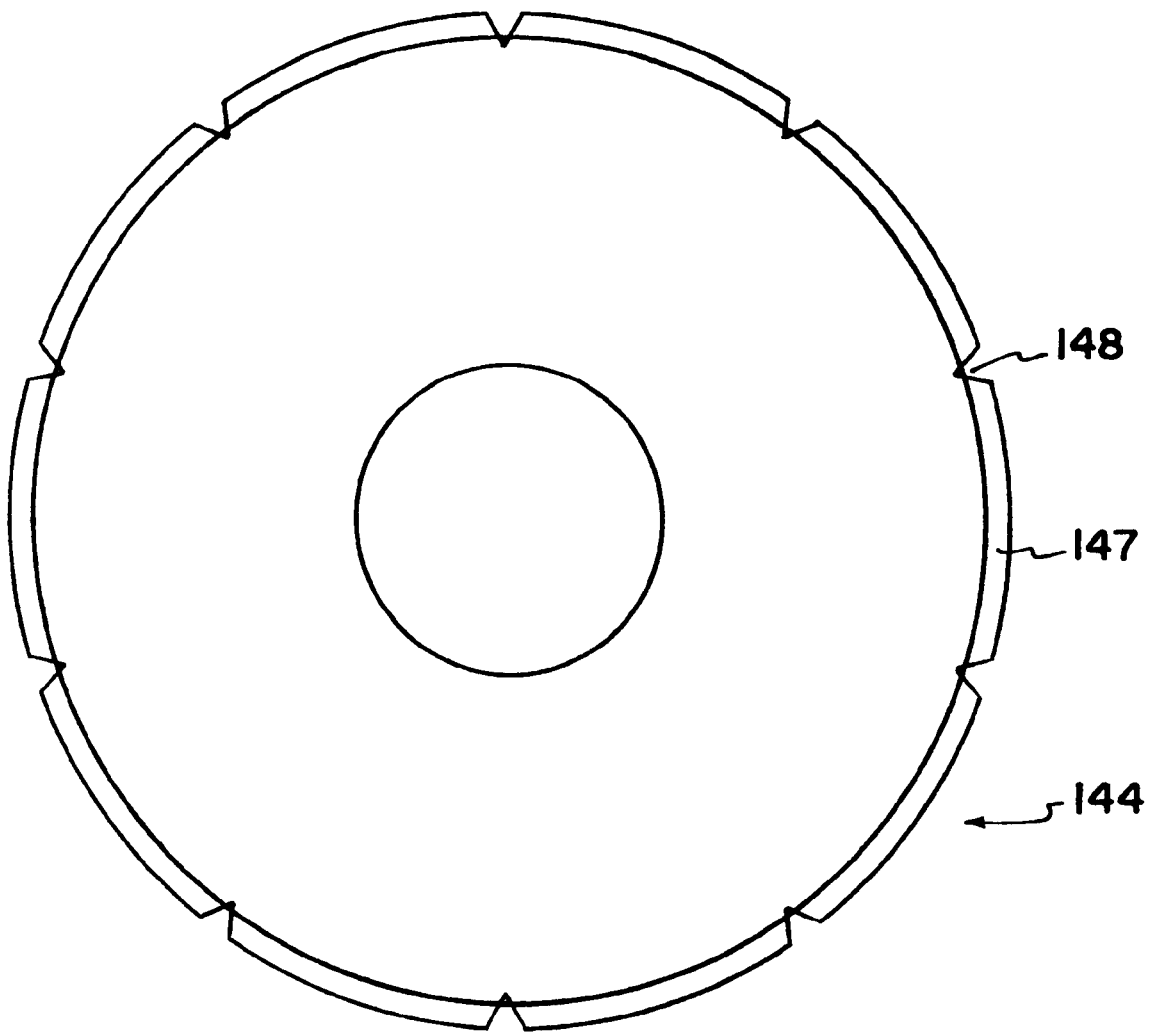
FIG. 10A is a plan view of a second version of a modified rotary blade for use in a cutter for forming the closure of the device of FIG. 1, with V-shaped interruptions or nicks and a different spacing than the blade of FIG. 9A.
Figure 10B:
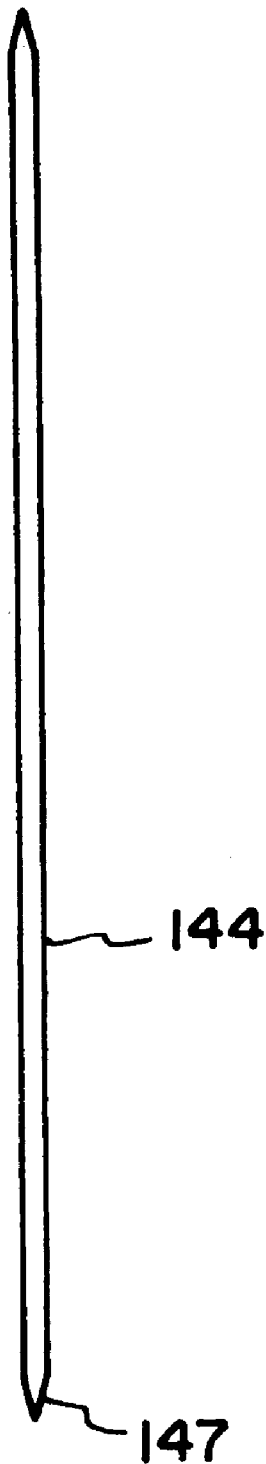
FIG. 10B is an end or profile view of the modified rotary blade of FIG. 10A.
Figure 11A:
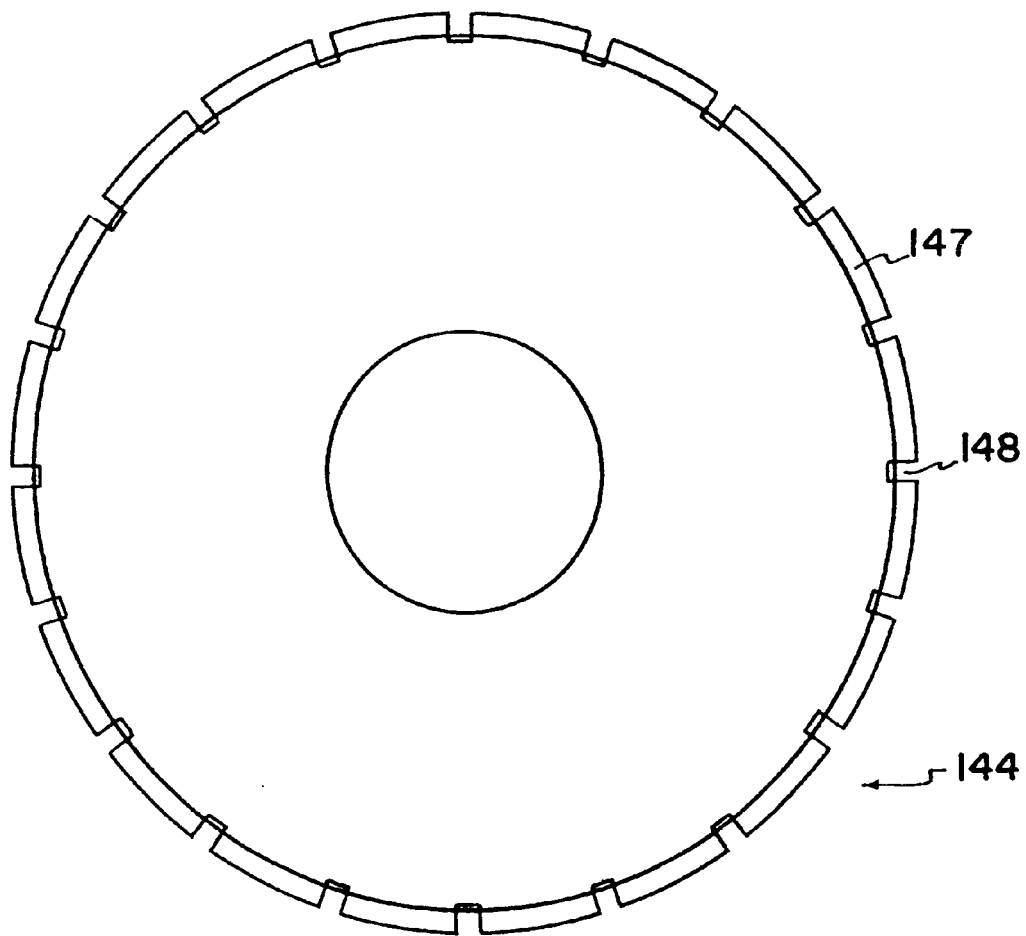
FIG. 11A is a plan view of a third version of a modified rotary blade for use in a cutter for forming the closure of the device of FIG. 1, with substantially rectilinear interruptions or nicks.
Figure 11B:
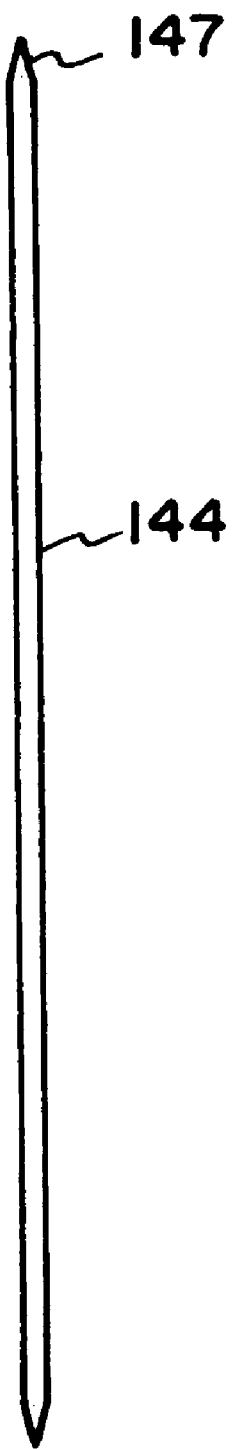
FIG. 11B is an end or profile view of the modified rotary blade of FIG. 11A.
Figure 12A:
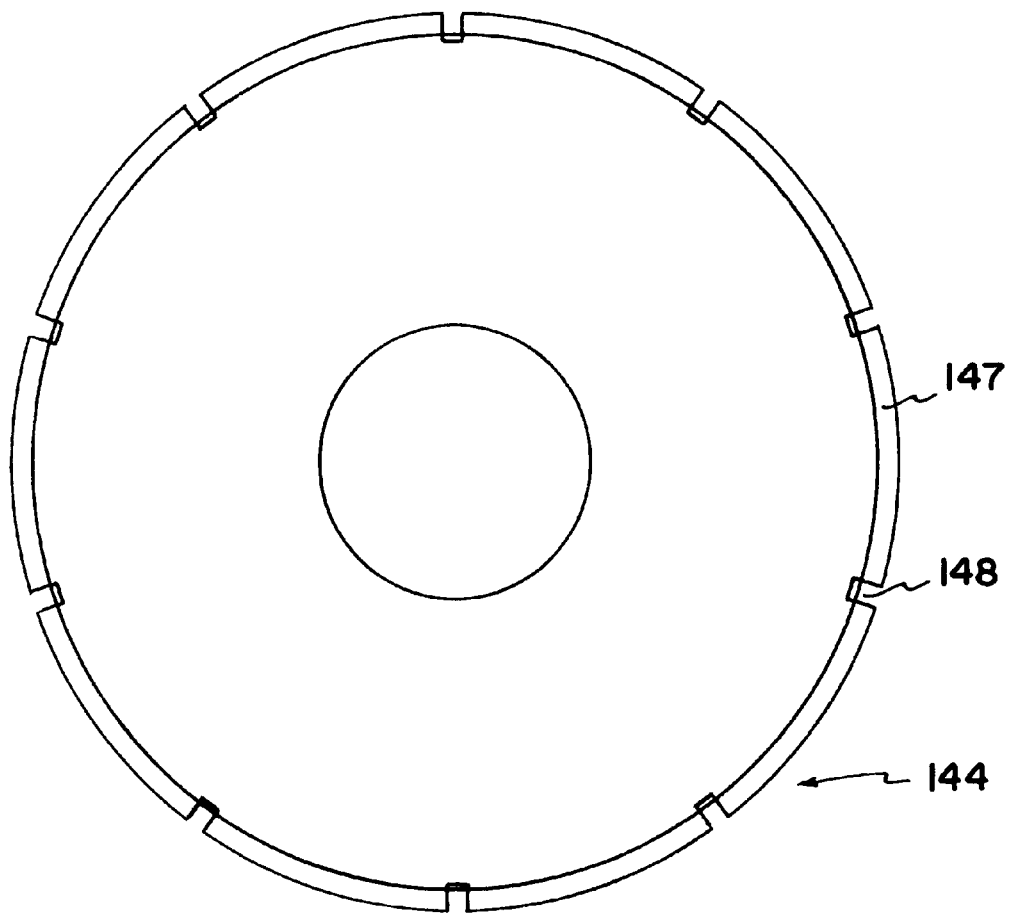
FIG. 12A is a plan view of a fourth version of a modified rotary blade for use in a cutter for forming the closure of the device of FIG. 1, with substantially rectilinear interruptions or nicks and a different spacing than the blade of FIG. 11A.
Figure 12B:
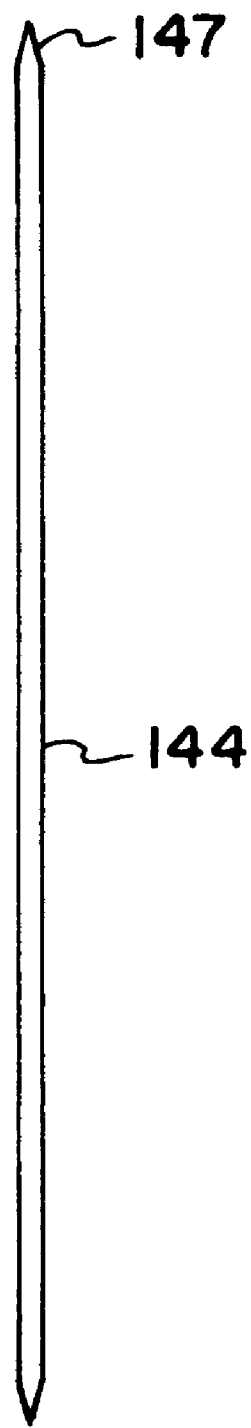
FIG. 12B is an end or profile view of the modified rotary blade of FIG. 12A.

The rotary blade 144 is preferably a modified double bevel buffed lark blade available from Blade Tech, Inc. and has an outer diameter of 62 mm. and a thickness of 0.012 inch. Various suitable modifications of the blade 144 are shown in FIGS. 9A–12A and 9B–12B, showing the bevel 147 and various sizes, spacings, shapes, and angles of the nicks or interruptions 148. FIGS. 9A, 10A, 11A and 12A show plan views of the blade 144, while FIGS. 9B, 10B, 11B, and 12B show end or profile views of the blade 144. In FIGS. 9 and 10, an angled nick or interruption is shown with two possible spacings, one in FIG. 9 and a second in FIG. 10. In FIGS. 11 and 12, a substantially rectilinear nick or interruption is shown with two possible spacings, one in FIG. 11 and a second in FIG. 12. Other shapes of the nicks or interruptions can also be used.

The blade assembly 140 can be adjusted to vary the angle of the rotary blade 144 with respect to the base 122 by loosening adjustment screws 149 and the angle can be gauged by means of an angle selection gauge 150.

Although a modified double bevel rotary blade 144 is described herein, a single bevel blade can also be used to make the required cut in forming a closure such as the closure 40. Furthermore, although the bevel cutter 120 is a manually operated device and suitable for cutting one or relatively few testing devices at one time, the bevel cutter 120 can be enlarged to allow a larger number of devices to be cut at one time, and the cutting edge can be moved by suitable means such as a pneumatic cylinder, or an electric motor. Also, automated cutting means can be used to cut and thus form a closure in accordance with the present invention with sheet-fed or web-fed stock, and other cutting means such as a straight-edge blade modified to provide the nicks or bridges required, or a laser can be employed to form a cut. Other cutting methods such as knife-edge cutting can also be used. Such cutting methods are well known in the art and need not be set forth in further detail here.

To form the closure 40, the testing device 20 is placed on the base 122 as shown by outline 160 (FIG. 6) with the front panel 22 up and the adhesive 110 proximate to the straight edge 126. The vertical adjustment knob and screw 142 are adjusted so that the depths of the cut formed by the modified rotary blade 144 is through the front panel. The angle of the modified rotary blade 144 is adjusted to the appropriate angle, which in the embodiment disclosed herein is an angle 152 of less than 90° and preferably as recited above. With the testing device 20 in place, as shown by the outline 160, the testing device 20 is held firmly against the guard 126 and the cutting head 136 is moved along the linear rails 130 and 132 parallel to the edge of the guide 126, thereby forming a cut through the front panel 22 proximate but not over the adhesive 110, thereby defining the closure 140 and the fixed member 46.

In particular, the interrupted beveled edge 42 (FIG. 3) and the undercut edge 44 are formed, defining a beveled angle 170 and an undercut angle 172 equal to the angle set by the modified rotary blade 144. Thus, the beveled angle 170 and the undercut angle 172 are equal, and are less than 90°. Typically, the bevel angle is between about 5° to about 30° from the vertical, or about 65° to about 85°. Preferably, the angle is from about 6° to about 15° from the vertical, or about 75° to about 84°. More preferably, the angle is from about 8° to about 10° from the vertical, or about 80° to about 82°. The undercut angle 172 is supplementary to a fixed member 174 formed by the fixed member 46; that is, the undercut angle 172 and the fixed member 174 together total 180°. Thus, the bevel angle 170 and the fixed member angle 174 are likewise supplementary.

In determining the angle of the cut made to form the closure 40 or other closures in accordance with the present invention, factors to be considered include the degree of hold desired when the interrupted bevel edge 42 is retained under the undercut edge 44, the thickness of the members or panels that form the interrupted bevel and undercut edges, the amount of internal pressure to be applied between opposing test elements carried within a testing device utilizing the closure, the hinge design (if a hinge is employed in the device), the material or materials from which the device is made, the characteristics of the chromatographic medium, and the presence or absence of other incorporated elements such as a receptacle for a sample holder such as a swab, and other factors. In general, any angle less than 90° can be operable and thus within the scope of the invention, provided that the protruding corner 48 is capturable beneath the overhanging corner 50 to thus close the testing device, and that the interrupted beveled edge 42 can be released from the undercut edge 44 to open the device. Preferred angles are recited above.

Preferably, the adhesive 110 is near the closure 40, and preferably as close as reasonably feasible to prevent gaping or bowing between a fixed member 46 and the back panel 24 as the testing device 20 is opened, pulling the interrupted beveled edge 42 from beneath the undercut edge 44. Such bowing may, for example, deform the fixed member 46, and thus vary the force applied between the opposing testing elements when the device 20 is closed. This variation of the force is to be avoided.

With the testing device 20 formed from SBS, it is preferred that the moisture content of the SBS material is fixed or stabilized prior to the formation of the closure 40 by means of the bevel cutter 120. This may be accomplished, for example, by placing the device in a vacuum chamber. Preferably the moisture content of the testing device 20 is stabilized at approximately 1% prior to the formation of the closure 40, although other moisture contents are also possible and yield a functioning closure in accordance with the present invention. It is also to be clearly understood that the closure of the present invention is operable without the moisture content of the testing device 20 being stabilized prior to forming the closure 40. However, moisture stabilization is preferred, although not necessarily required, and provides a more predictable and reliable operation of the closure 40 by equalizing and distributing stresses throughout the device before the cut is made and thus decreasing the likelihood of improperly aligned edges 42 and 44.

With the closure 40 formed as just described, the testing device 20 can be packaged in a hermetically sealed envelope (not shown) for storage and transportation prior to use.

In use, the device is removed from its protective envelope (not shown) and is opened as described above. For the embodiment shown in FIG. 4, a buffer is added to the labeled applicator 70 and a sample that may contain antibodies to *Helicobacter pylori* is applied to the sample application zone 62. After a time sufficient to allow the sample to flow through the chromatographic medium 60 to the conductor 64 and during which any anti-*H. pylori* antibody is bound to the first line of immobilized component 66, the device 20 is closed by means of the closure 40 as described above. The absorber 72 is placed into contact with the sample application pad 62 and the absorber 72. Any immobilized analyte bound to the first line of immobilized component 66 in turn immobilizes labeled reagent, producing a colored or otherwise visible line. Further, the labeled reagent is also bound to the second line of immobilized component 68 to demonstrate the operability of the test device 20 and the correct performance of the test. The results of the test, including the presence or absence of label at the first and second lines 66 and 68, are observed through the window 28.

Figure 5A:
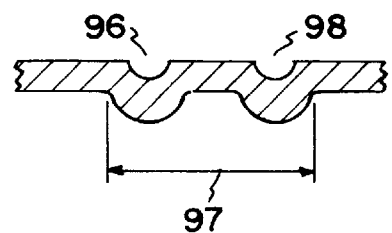
FIG. 5A is a section view of the hinge portion of the blank of FIG. 5 taken along line 5A—5A thereof.
Figure 5B:
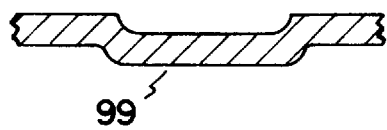
FIG. 5B is a section view of an alternative hinge portion useful in the device of FIG. 1.
Figure 6:
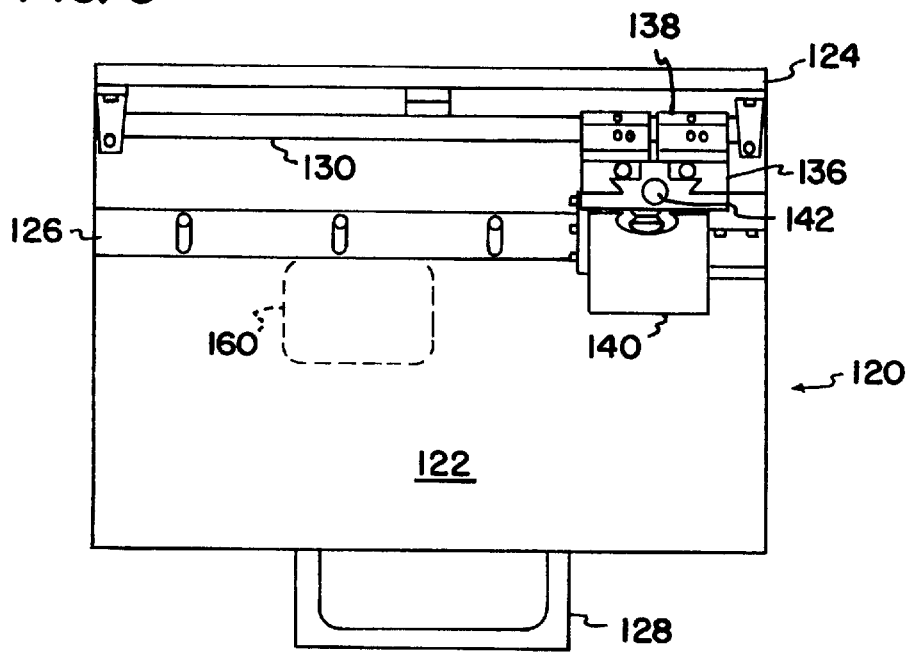
FIG. 6 is a top view of a bevel or closure cutter suitable for forming the closure of the device of FIG. 1.
Figure 7:
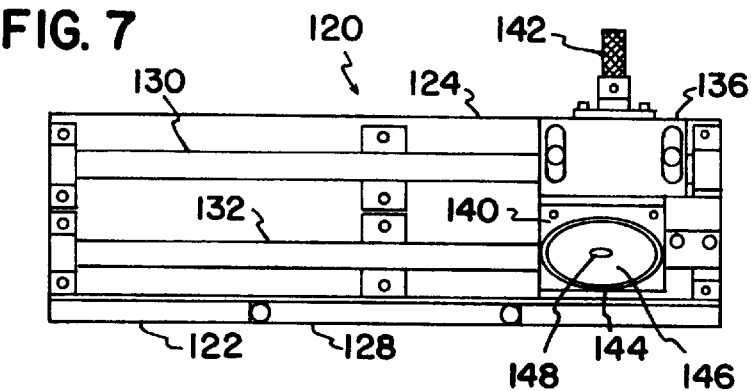
FIG. 7 is a front view of the cutter of FIG. 6.
Figure 8:
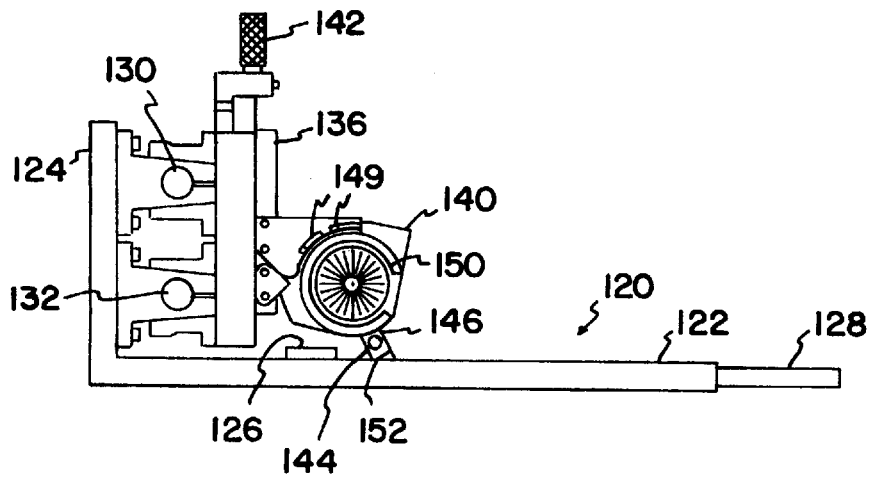
FIG. 8 is a side view of the cutter of FIG. 6.

The hinge structure as illustrated in the cross-section embodiment of FIGS. 5A and 5B, and preferably the structure of FIG. 5B, provides stable and consistent hinges that suitably align the interrupted beveled edge 42 with the undercut edge 44. It is to be appreciated that if the front panel 22 is offset by, for example, instability of the hinge 26, and the interrupted beveled edge 42 moves away from the undercut edge 44, sufficient movement of this nature will prevent the protruding corner 48 from engaging the overhanging corner 50 and cause the closure 40 to fail.

Conversely, if the front panel 22, with the device 20 in its open state, is offset such that the protruding corner 48 substantially overlaps the fixed member 46, it is likely that the closing pressure applied to the front and back panels 20 and 24 will not engage the closure 40.

Thus, the relatively stable hinge designs of FIGS. 5A and 5B, and particularly that of FIG. 5B, provide two forms of suitable hinges for the present invention. Such designs also enable the distance from the front panel 22 to the back panel 24 to be controlled when the testing device 20 is in its closed condition by varying the distance between the parallel crease rules 96 and 98 of FIG. 5A or the overall width of the single wide crease rule 99 of FIG. 5B. This is particularly advantageous for accommodating various thicknesses of testing elements, such as chromatographic media, sample application zones, and other testing elements, contained within the testing device 20 and also accommodating the amount of pressure that is applied between opposing testing elements to bring and hold them in operable contact as may be required by the characteristics of the testing materials and the like.

Other hinged designs, such as a rounded hinge, may be similarly suitable and will be apparent to those skilled in the art without undue experimentation.

With the present device of FIG. 1, the length of the closure 40 of the device of FIG. 1 can be, for example, approximately 3 inches (7.5 mm) although the size of the device employing the closure in accordance with the present invention can, of course, be adapted over a wide range according to the particular needs of the user, including the analyte to be assayed, the volume of the test sample, the volume of labeled and unlabeled specific binding partners required, the flow characteristics of the chromatographic medium, and other characteristics well known to those skilled in the art.

The width of a testing device in accordance with the present invention, and particularly the width of, for example, the front panel 22 (between the closure 40 and the hinge 26) can be varied according to the needs of the testing elements disposed within the testing device. For example, chromatographic medium 60 and related testing elements on the front and back panels 22 and 24 can be collectively moved toward or away from the closure 40. It is also to be appreciated that although the closure 40 of the testing device 20 is shown as extending the entire length of the device, only a portion of the front panel 22 edge could be formed to define the closure 44 as the needs of the testing device 20 dictate. Further, the length of the front panel 22 (the dimension parallel to the closure 40) needs, of course, to correspond to the entire length of the back panel 24 as illustrated with respect to the embodiment described for testing device 20.

Another form of a testing device employing the closure of the present invention is illustrated in FIGS. 13 and 14. Such a testing device 200, which can be suitable for testing of hemoglobin, and, for example, fecal specimens, includes a front panel 202 and a back panel 204. A closure in accordance with the present invention is formed by an interrupted beveled edge 206 formed in an outer edge of the front panel 202 and an undercut edge 208 on a fixed member 210. The interrupted beveled edge has uncut regions or bridges 207 as described above. A hinge 212 is defined between the front and back panels 202 and 204. In this embodiment, a plurality of sample application pads 220, 222, and 224 are disposed on the inside of the back panel 204 proximate to the hinge 212, and a corresponding plurality of chromatographic testing members 226, 228, and 230 are disposed on the inside of the front panel 202. Each of the testing members 226, 228, and 230 includes a chromatographic medium 232, a labeled reagent pad 234, a transfer pad 236 aligned to contact a corresponding sample application pad, such as pad 220, when the testing device is closed, and an absorber 238 at a second end of the chromatographic medium 232.

Windows 240, 242, and 246 are formed in the front panel 202 in alignment with the chromatographic testing members 226, 228, and 230 so as to allow observation of test results. A reduced width portion 246 of the back panel 204 allows the front panel 202 to be easily lifted away from the back panel 204 to open the testing device 200.

In use, the testing device 200 is opened, samples that may contain an analyte of interest, such as hemoglobin, are applied to the sample application pads 220, 222, and 224, and the device is closed by pressing the front and back panels 202 and 204 together, thus engaging the interrupted beveled edge 206 beneath the undercut edge 208. The samples flow through the chromatographic testing members 226, 228, and 230, performing, for example, an immunochemical assay on the samples to thereby indicate the presence or absence of hemoglobin in the samples. The presence of hemoglobin can be indicated by means of visible lines appearing in windows 240, 242, and 244. Such testing devices are similar to the hemoglobin testing device described in the above-referenced U.S. patent application, Ser. No. 07/888,831.

The testing device can be formed in a manner and by a process similar to that described above with respect to the testing device 20 for the embodiment of the testing device 200 of FIGS. 13 and 14. Alternatively, a device similar to that of FIGS. 9 and 10 can be constructed that only performs one assay on one sample.

The same principles can be used to construct assay devices for other analytes that operate by a sandwich immunoassay principle, performing a unidirectional assay.

A further embodiment of a testing device incorporating the enclosure of the present invention is illustrated in FIG. 15. A testing device 300 includes a front panel 302 and a back panel 304 joined by hinge 306. Closures in accordance with the present invention are formed by interrupted beveled edges 308 and 310 on opposite edges of the front panel 302, and corresponding undercut edges 312 and 314 formed by corresponding planar fixed members 316 and 318 which are proximate to corresponding edges of the back panel 304. The interrupted beveled edges 308 and 310 have uncut regions or bridges 309 and 311 as described above. As a further alternative, the hinge 306 can be eliminated, thus enabling the front panel 302 to be completely removable from the device 300. In either alternative, such a testing device can include testing elements (not shown) for sample analysis, particularly by an immunochemical assay. This can be in a unidirectional format, a bidirectional format, or a split-flow format.

A further alternative of a device in accordance with the present invention is a testing device 340 shown in FIG. 16. The device 340 includes a front panel 342 and a back panel 344, seen by way of a cutaway portion of the front panel 342 in FIG. 16. The front and back panels 342 and 344 are joined at a hinge 346. A first and second closure 348 and 350, both as described above with reference to the other embodiments disclosed herein, meet at a right angle 352. The device 340 can include testing elements similar to those described with respect to the testing device 20 and testing device 200, or other testing devices. These testing elements can be arranged to perform a unidirectional sandwich immunoassay, a bidirectional immunoassay for the detection of an antibody, or a split-flow immunoassay.

Another form of the present invention is illustrated in FIG. 17, wherein a device 360 is similar to the device of FIG. 1, including a front panel 362, a back panel 364, and a closure in accordance with the present invention defined by an interrupted beveled edge 366 and an undercut edge 368. The interrupted beveled edge has one or more uncut regions or bridges 367. A portion 370 of the front panel 362 extends beyond the interrupted beveled edge 366 thus hiding the closure formed by the edges 366 and 368 when the front and back panels 362 and 364 are closed. This device can again be used to perform a unidirectional sandwich immunoassay, a bidirectional immunoassay where an antibody is an analyte, or a split-flow immunoassay as described above.

Additional alternatives of a closure in accordance with present invention are illustrated in FIGS. 18A, 18B, and 18C. FIG. 18A depicts a cross-section through the closure in a region that is not uncut and does not form a bridge. In FIG. 18A, a closure 400 formed by a fixed or retaining member 402 and a movable or retained member 404 includes an angle portion 406 and a perpendicular portion 408 that is perpendicular to a base member 410. FIG. 18B depicts a cross-section through the closure in a region that is uncut, showing the bridge 411.

FIG. 18C depicts a cross-section through the closure in a region that is not uncut and does not form a bridge. In FIG. 18C, a closure 420 is formed by a fixed or retaining member 422 and a movable or retained member 424 that includes an angled portion 426 proximate to a base member 428 and a perpendicular portion 430. In the embodiment of FIG. 18C, the fixed or retaining member 422 includes a double interrupted beveled edge 432.

Figure 18D:
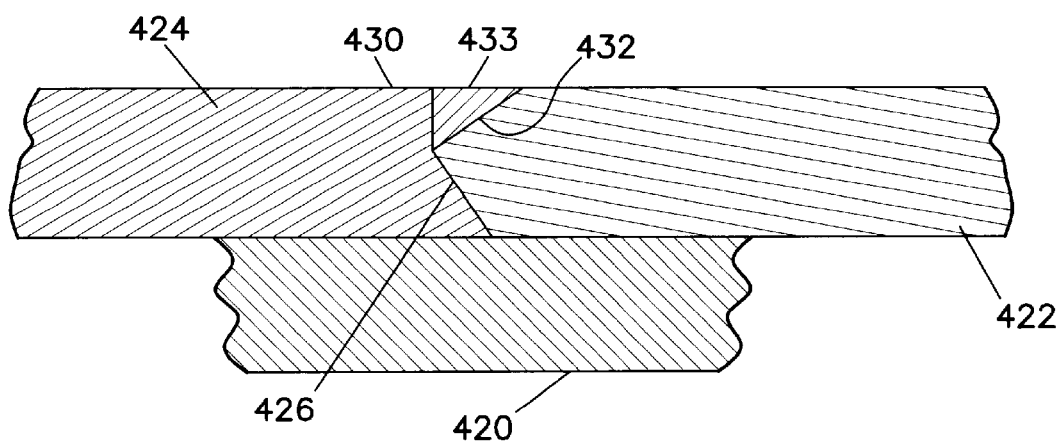
FIG. 18D depicts a cross-sectional view through the interrupted bevel closure of FIG. 18C in a portion that has uncut regions forming bridges.

FIG. 18D depicts a cross-section through the same closure shown in FIG. 18C through a region that is uncut and showing a bridge 433.

Figure 18E:
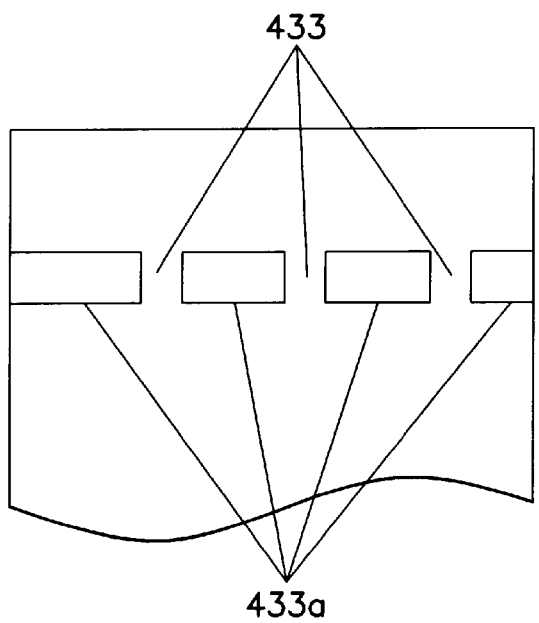
FIG. 18E depicts a top view of the interrupted bevel closure of FIGS. 18C and 18D showing the bevel closure interrupted by uncut regions forming bridges.

FIG. 18E depicts a top view of the closure of FIGS. 18C and 18D, showing the bridges 433 and the regions 433a that are cut and that do not form a bridge.

Figure 18F:
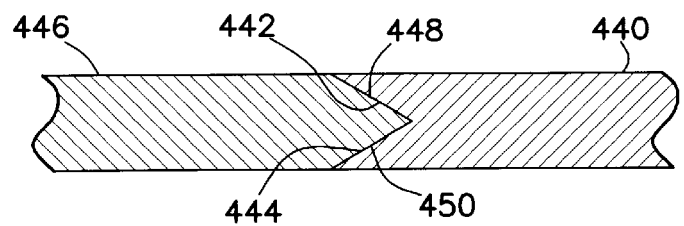
FIG. 18F illustrates yet another alternative form of a closure in accordance with the present invention employing an interrupted bevel closure, depicted in cross-sectional view through a portion of the bevel closure that does not have uncut regions forming bridges.
Figure 18G:
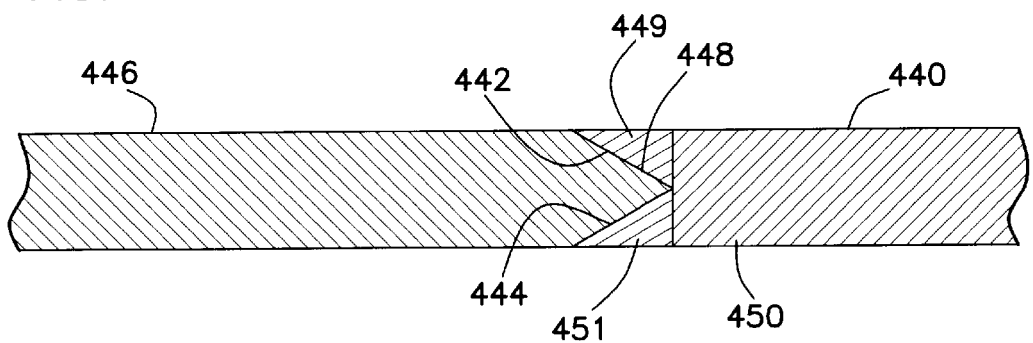
FIG. 18G depicts a cross-sectional view through the interrupted bevel closure of FIG. 18F in a portion that has uncut regions forming bridges.

FIGS. 18F and 18G depict another embodiment of a closure according to the present invention. FIG. 18F depicts a cross-section through the closure in a region that is not uncut and does not form a bridge. With respect to FIG. 18F, a first member 440 includes a double angled edge having angled surfaces 442 and 444. A second member 446 with a double interrupted beveled edge having surfaces 448 and 450, can be retained by the angled surfaces 442 and 444. FIG. 18G depicts a cross-section through the same closure in a region that forms bridges 449 and 451.

It is to be appreciated that the embodiments of FIGS. 18A and 18C do not require the base member 410 or the base member 428, respectively, if further displacement of the movable or retained members 404 or 424 downwardly as viewed in FIGS. 18A or 18C is not important. Further, the embodiment of FIG. 18F enables the second member 446 to be captured by the first member 440 (or vice versa) regardless of whether the second member 446 approaches the first member 440 from above or below the first member 440 as viewed with respect to FIG. 18F. It is to be appreciated that "above" and "below" is used in the description of the embodiments of FIGS. 18A through 18G is relative with respect to such Figures and should not be deemed as limitations with respect to the design or operability of the present invention.

Another embodiment of a device according to the present invention is shown in FIG. 19. Such a device 470 includes a cover 472 and a base 474 joined by a hinge 476. Outer corners of the base 474 include retaining members 478 and 480 that include undercut edges 482 and 484. Corresponding interrupted beveled edges 486 and 488 on corresponding corners of the cover 472 cooperate with the undercut edges to form a closure in accordance with the present invention. The interrupted beveled edges 486 and 488 have uncut regions or bridges 487 and 489. The device 470 can include testing elements similar to those above, to perform a unidirectional sandwich immunoassay, a bidirectional immunoassay, the assay of an antibody analyte, or a split-flow immunoassay.

ADVANTAGES OF THE PRESENT INVENTION

An advantage of the closure of the present invention, particularly with respect to testing devices and devices as described herein, is that the closing force is equally distributed along the length of the closure, such as the closure 40 in the testing device 20. This is to be compared with, for example, closing techniques such as strips of peelable tape, hook-and-loop fasteners, snaps, or tabs. Additionally, the modified bevel closure of the present invention also provides a more secure closure with a shallower cut than previous closures. This facilitates the ease of closure and ensures a secure closure during shelf life up to the point of use and during use. This prevents inadvertent opening of the test device while the assay is being performed. Various alternatives are also within the scope of the present invention. For example, although the devices described herein are described with respect to SBS paper board material, other materials can also be used as alternatives, such as plastic. Furthermore, a single material thickness of material or more than two thicknesses of material are also useable, rather than two thicknesses of material for the device. Additionally, a closure in accordance with the present invention can be curved or curving in addition to the straight or linear closures disclosed herein. Additionally, the closure in accordance with the present invention can be used on other than test devices, such as on envelopes, boxes, other containers, and the like. Other suitable means for positioning, for example, the front and back panels 22 and 24 of the device 20 include other forms of mechanical hinges or hinges formed separately from the device and that are fixed to the device to provide the positioning function, and other flexible materials such as a tape.

Although the present invention has been described in considerable detail, with reference to certain preferred versions thereof, other versions and embodiments are possible. Therefore, the scope of the present invention is determined by the following claims.

We claim:

1. A reclosable testing device, comprising:
   (a) abase member;
   (b) a cover member;
   (c) a fixed member fixed to the base member, the fixed member having an undercut edge;
   (d) a hinge between the base member and the cover member;
   (e) a testing element fixed to at least one of the base member or the cover member; and
   (f) closure means comprising an interrupted beveled edge on the cover member, the interrupted beveled edge being supplementary to the undercut edge and being adapted to be received and retained in a closed position with the undercut edge of the fixed member in an edge-to-edge engagement, the base member, the cover member, and the fixed member being formed of a sufficiently rigid material to minimize bowing on the closure thereby to ensure that a sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means; and wherein the beveled edge is interrupted with at least one uncut bridge region to increase the force required to separate the base member and cover member.

2. The testing device of claim 1 wherein the device includes a testing element fixed to the base member.

3. The testing device of claim 1 wherein the device includes a testing element fixed to the cover member.

4. The testing device of claim 1 wherein the cover member and the fixed member extend respectively between extremities defined between ends, the beveled edge on the cover member extending from about one end of the cover member to about the opposite end of the cover member, and the supplementary undercut edge extending from about one end of the fixed member to about the opposite end of the fixed member.

5. The testing device of claim 1 including a testing element fixed to the base member and a testing element fixed to the cover member, whereby when the beveled edge is in a closed position there is closure force for effecting transfer of a fluid between the test elements, and wherein the beveled edge and the supplementary undercut edge are positioned and aligned from the hinge at least about opposite the test elements where the fluid transfers between the test elements.

6. The testing device of claim 1 further including an extension portion of the cover member extending beyond the beveled edge, the extension portion covering a line of closure formed by the beveled edge and the undercut edge when the cover member and the fixed member are closed.

7. The testing device of claim 1 including a first testing element fixed to the base member and a second testing element fixed to the cover member.

8. The testing device of claim 7 wherein the first testing element and the second testing element are opposable and are brought into operable contact when the cover member is closed and retained by the closure means.

9. The testing device of claim 8 wherein either the first testing element or the second testing element includes a chromatographic medium.

10. The testing device of claim 8 wherein either the first testing elements or the second testing element includes a sample application zone.

11. The testing device of claim 9 wherein either the first testing element or the second testing element includes a sample application zone, and wherein the chromatographic medium and the sample application zone are not both located on either the first testing element or the second testing element such that the sample application zone and the chromatographic medium are brought into operable contact when the cover member is closed and retained by the closure means.

12. The testing device of claim 1 wherein the device includes at least two bridges.

13. The testing device of claim 12 wherein the bridges are located in a region that is substantially less than the entire contact area between the cover member and the fixed member.

14. The testing device of claim 12 wherein the bridges are located in a region that spans substantially the entire contact area between the cover member and the fixed member.

15. The testing device of claim 1 wherein the angle of the bevel is between about 5 degrees to about 30 degrees from the vertical.

16. The testing device of claim 15 wherein the angle of the bevel is between about 6 degrees to about 15 degrees from the vertical.

17. The testing device of claim 16 wherein the angle of the bevel is from about 8 degrees to about 10 degrees from the vertical.

18. A reclosable testing device comprising:
   (a) a base member;
   (b) a cover member;
   (c) fixed members fixed to the base member, each fixed member of the fixed members having an undercut edge;
   (d) a hinge between the base member and the cover member;
   (e) a testing element fixed to at least one of the base member or the cover member; and
   (f) closure means comprising interrupted beveled edges on the cover member, the beveled edges being supplementary to the undercut edges and being adapted to be received and retained in a closed position with the undercut edges of the fixed members in an edge-to-edge engagement, the base member, the cover member, and the fixed members being formed of a sufficiently rigid material to minimize bowing on the closure thereby to ensure that a sample for testing and the testing element come into operable contact for effecting a test, and that a force is distributed substantially evenly over the cover member, thereby further ensuring that, together with the hinge between the base member and the cover member, and with the closure means, the closure force is substantially equally distributed along the length of the closure means; and wherein the beveled edges are interrupted with at least one uncut bridge region to increase the force required to separate the base member and the cover member.

19. The testing device of claim 18 including a testing element fixed to the base member and a testing element fixed to the cover member, whereby when the beveled edge is in a closed position there is a closure for effecting transfer of a fluid between the testing elements, wherein at least one portion of the interrupted beveled edge and one portion of the undercut edge are positioned and aligned from the hinge at least about opposite the test elements where the fluid transfers between the test elements, and another portion of the interrupted beveled edge and another portion of the undercut edge are located at a position removed from the element where the fluid transfers between the test elements.

20. The testing device of claim 18 wherein the hinge between the base member and the cover member and wherein the fixed members and the cover member respectively include corners remote from the hinge wherein the undercut edges and the beveled edges respectively are located at the corners, and not between the respective corners.

21. The testing device of claim 18 wherein the base member includes opposite ends directed transversely from the hinge, and includes a fixed member located at each respective end and the beveled edges are located respectively at the opposite ends, thereby to constitute closures on at least two sides of the device.

22. The testing device of claim 18 wherein the base member includes an adjacent end directed transversely from the hinge and a side opposite the hinge and the beveled edge and the undercut edge are located respectively at the adjacent end and the opposite end, thereby to constitute closures on at least two sides of the device.

23. The testing device of claim 18 wherein the device includes a first testing element fixed to the base member and a second testing element fixed to the cover member.

24. The testing device of claim 23 wherein the first and second testing elements are opposable when the cover member is closed and retained by the closure means.

25. The testing device of claim 24 wherein either the first testing element or the second testing element includes a chromatographic medium.

26. The testing device of claim 25 wherein either the first testing element or the second testing element includes a sample application zone.

27. The testing device of claim 26 further including a chromatographic medium and wherein the chromatographic medium and the sample application zone are not both located on either the first testing element or the second testing element.

28. The testing device of claim 18 wherein the interrupted bevel closure includes at least two bridges.

29. The testing device of claim 28 wherein the bridges are located in a region that spans substantially less than the entire contact area between the cover member and the fixed members.

30. The testing device of claim 28 wherein the bridges are located in a region that spans substantially the entire contact area between the cover member and the fixed members.

31. The testing device of claim 18 wherein the angle of the bevel is between about 5 degrees to about 30 degrees from the vertical.

32. The testing device of claim 31 wherein the angle of the bevel is between about 6 degrees to about 15 degrees from the vertical.

33. The testing device of claim 32 wherein the angle of the bevel is between about 8 degrees to about 10 degrees from the vertical.

34. A reclosable testing device comprising:
  (a) a base member;
  (b) a cover member having an interrupted beveled edge;
  (c) a fixed member fixed to the base member, the fixed member having an undercut edge being supplementary to the interrupted beveled edge;
  (d) a hinge between the base member and the cover member, wherein the closure of the cover member on the base member effects engagement of the interrupted beveled edge with the undercut edge of the fixed member forming a means for closure, the interrupted beveled edge being adapted to be received and retained in a closed position in an edge-to-edge engagement with the undercut edge of the fixed member;
  (e) a testing element fixed to the base member and a testing element fixed to the cover member, the testing elements being in operable contact when the cover member and the base member are closed, the base member, the cover member, and the fixed member being formed of a sufficiently rigid material to minimize bowing on the closure thereby to ensure that a sample for testing and at least one of the testing elements come into operable contact for effecting a test, and that a force is distributed substantially evenly over the cover member, thereby further ensuring that, together with the hinge between the base member and the cover member, and with the closure means formed by closure of the cover member on the base member, the closure force is substantially equally distributed along the length of the closure means; and wherein the beveled edge is interrupted with at least one uncut bridge region to increase the force required to separate the base member and the cover member.

35. The testing device of claim 34 wherein the cover member and fixed member are extended respectively between extremities defined between ends, the beveled edge of the cover member extending from about one edge of the cover member to about the opposite end of the cover member, and the supplementary undercut edge extending from about one end of the fixed member to about the opposite end of the fixed member.

36. The testing device of claim 34 wherein the interrupted beveled edge and the supplementary undercut edge are positioned and aligned from the hinge at least about opposite the test elements.

37. The testing device of claim 34 further including an extension portion of the cover member extending beyond the beveled edge, the extension portion covering a line of closure formed by the interrupted beveled edge and the undercut edge when the cover member and the fixed member are closed.

38. The testing device of claim 34 wherein one of the testing element fixed to the base member and the testing element fixed to the cover member is a chromatographic medium and the other of the testing element fixed to the base member and the testing element fixed to the cover member is a sample application zone.

39. The testing device of claim 35 wherein the interrupted beveled closure has at least two bridges.

40. The testing device of claim 39 wherein the bridges are located in a region that spans substantially less than the entire contact area between the cover member and the fixed member.

41. The testing device of claim 39 wherein the bridges are located in a region that spans substantially all of the entire contact area between the cover member and the fixed member.

42. The testing device of claim 34 wherein the angle of the bevel is between about 5 degrees to about 30 degrees from the vertical.

43. The testing device of claim 42 wherein the angle of the bevel is from about 6 degrees to about 15 degrees from the vertical.

44. The testing device of claim 43 wherein the angle of the bevel is between about 8 degrees to about 10 degrees from the vertical.

45. A reclosable testing device comprising:
(a) a base member;
(b) a cover member having interrupted beveled edges;
(c) fixed members fixed to the base member, the fixed members having undercut edges, the undercut edges being supplementary to the interrupted beveled edges such that in a closed position of cover member and base member the interrupted beveled edges of the undercut edges are in edge-to-edge alignment forming a means for closure;
(d) a hinge between the base member and the cover member; and
(e) a testing element fixed to the base member and a testing element fixed to the cover member, the testing elements being in operable contact when the cover member and the base member are closed, the base member, the cover member, and each of the fixed members being formed of a sufficiently rigid material to minimize bowing on the closure, thereby to ensure that a sample for testing and at least one of the testing elements come into operable contact for effecting a test, and that a force is distributed substantially evenly over the cover member, thereby further ensuring that, together with the hinge between the base member and the cover member, and with the means for effecting closure of the cover member on the base member, the closure force is substantially equally distributed along the length of the closure means; and wherein the beveled edge is interrupted with at least one uncut bridge region to increase the force required to separate the base member and the cover member.

46. The testing device of claim 45 wherein the base member includes opposite ends directed transversely from the hinge, and includes fixed members located at each respective end and the interrupted beveled edges and undercut edges are located respectively at the opposite ends, and further including an elongated chromatographic medium with at least one of the elements for fluid to traverse the chromatographic medium in a defined flow path.

47. The testing device of claim 46 wherein the defined flow path is from a first end of the chromatographic medium to a second end of the chromatographic medium.

48. The testing device of claim 46 wherein the defined flow path is from a point removed from both a first end and a second end of the chromatographic medium toward both the first end and the second end of the chromatographic medium.

49. The testing device of claim 45 wherein the base member includes an adjacent end located transversely from the hinge, and includes a side opposite the hinge, and the interrupted beveled edges and the undercut edges are located respectively at the adjacent end and the opposite side and including an elongated chromatographic medium with at least one of the test elements for fluid to traverse the chromatographic medium in a defined flow path.

50. The testing device of claim 49 wherein the defined flow path is from a first end of the chromatographic medium to a second end of the chromatographic medium.

51. The testing device of claim 49 wherein the defined flow path is from a point removed from both a first end and a second end of the chromatographic medium toward both the first end and the second end of the chromatographic medium.

52. The testing device of claim 45 wherein when the interrupted beveled edge is in a closed position, a closure force is applied between the cover member and the fixed members, and wherein at least one portion of the interrupted beveled edge and one portion of the undercut edge are positioned and aligned from the hinge at least about opposite the test elements and another portion of the interrupted beveled edge and another portion of the undercut edge are located at a position removed from the elements, and wherein one of the test elements includes an elongated chromatographic medium for fluid to traverse the chromatographic medium.

53. The testing device of claim 52 wherein the defined flow path is from a first end of the chromatographic medium to a second end of the chromatographic medium.

54. The testing device of claim 52 wherein the defined flow path is from a point removed from both a first end and a second end of the chromatographic medium toward both the first end and the second end of the chromatographic medium.

55. The testing device of claim 52 including a window located in at least one of the base member and cover member, the window being aligned along the length of the chromatographic medium such that a test indication on the chromatographic medium is visible through the window when the base member and the cover member are in a closed position.

56. The testing device of claim 45 wherein the fixed members and the cover member respectively include corners remote from the hinge and where the undercut edges and the interrupted beveled edges are located at the corners and not between the respective corners, and including an elongated chromatographic medium with at least one of the elements for fluid to traverse the chromatographic medium in a defined flow path.

57. The testing device of claim 56 wherein the defined flow path is from a first end of the chromatographic medium to a second end of the chromatographic medium.

58. The testing device of claim 56 wherein the defined flow path is from a point removed from both a first end and a second end of the chromatographic medium toward both the first end and the second end of the chromatographic medium.

59. The testing device of claim 56 including a window located in at least one of the base member and the cover member, the window being aligned along the length of the chromatographic medium such that a test indication on the chromatographic medium is visible through the window when the base member and cover member are in closed position.

60. The testing device of claim 45 wherein the interrupted bevel closure includes at least two bridges.

61. The testing device of claim 60 wherein the bridges are located in a region that spans substantially less than the entire contact area between the cover member and the fixed member.

62. The testing device of claim 61 wherein the bridges are located in a region that spans substantially the entire contact area between the cover member and the fixed member.

63. The testing device of claim 45 wherein the angle of the bevel is between about 5 degrees to about 30 degrees from the vertical.

64. The testing device of claim 63 wherein the angle of the bevel is from about 6 degrees to about 15 degrees from the vertical.

65. The testing device of claim 64 wherein the angle of the bevel is between about 8 degrees to about 10 degrees from the vertical.

66. A reclosable testing device comprising:
(a) a base member;
(b) a cover member;
(c) a fixed member fixed to the base member, the fixed member having an undercut edge;
(d) a hinge between the base member and the cover member;
(e) a testing element fixed to the base member and a testing element fixed to the cover member, at least one of the testing elements including an elongated chromatographic medium, and wherein one of the testing elements is arranged for receiving fluid and for transferring fluid to the testing element having the chromatographic medium, whereby the fluid is arranged to traverse the chromatographic medium along a defined flow path; and
(f) closure means comprising an interrupted beveled edge on the cover member, the interrupted beveled edge being supplementary to the undercut edge and being adapted to be received and retained in a closed position with the undercut edge of the fixed member in a edge-to-edge engagement, the base member, the cover member, and the fixed member being formed of a sufficiently rigid material to minimize bowing on the closure, and thereby to ensure that, together with the hinge between the base member and the cover member, and with the closure means, the closure force is substantially equally distributed along the length of the closure means whereby when the interrupted beveled edge is in the closed position, the closure force is distributed substantially uniformly between the cover member and the fixed member such that the fluid is effectively transferred between the testing elements and is enabled to effectively traverse the chromatographic medium; wherein the beveled edge is interrupted with at least one uncut bridge region to increase the force required to separate the base member and the cover member.

67. The testing device of claim 66 wherein the defined flow path is from a first end of the chromatographic medium to a second end of the chromatographic medium.

68. The testing device of claim 66 wherein the defined flow path is from a point removed from both a first end and a second end of the chromatographic medium toward both the first end and the second end of the chromatographic medium.

69. The testing device of claim 66 further including a window located in at least one of the base member and the cover member, the window being aligned along the length of the chromatographic medium such that a test indication on the chromatographic medium is visible through the window when the base member and the cover member are in a closed position.

70. The testing device of claim 66 wherein the base member and the cover member are formed from the same board material element and the hinge includes at least one crease formed in the board material, the board material having a thickness of about 0.024 inches.

71. The testing device of claim 66 wherein the base member and the cover member are planar elements formed from the same material element having a thickness and the hinge is formed along a crease line in the material and the test elements are located in adjacency on the cover member and the base member and the fixed member is mounted on a portion of the base member, such that in a position of closure, the cover member overlies the position of the base member not occupied by the fixed member, and the cover member and fixed member have edges in abutment, and wherein inward force is applied by the cover member and the base member on the test element substantially uniformly when the edge of the fixed member and the edge of the cover member are in edge-to-edge engagement.

72. The testing device of claim 66 wherein the interrupted beveled edge includes at least two bridges.

73. The testing device of claim 72 wherein the bridges are located in a region that spans substantially less than the entire contact area between the cover member and the fixed member.

74. The testing device of claim 72 wherein the bridges are located in a region that spans substantially the entire contact area between the cover member and the fixed member.

75. The testing device of claim 66 wherein the angle of the bevel is between about 5 degrees to about 30 degrees from the vertical.

76. The testing device of claim 75 wherein the angle of the bevel is from about 6 degrees to about 15 degrees from the vertical.

77. The testing device of claim 76 wherein the angle of the bevel is between about 8 degrees to about 10 degrees from the vertical.

78. A reclosable chromatographic testing device comprising:
(a) a base member;
(b) a cover member;
(c) fixed members fixed to the base member, each of the fixed members having an undercut edge;
(d) a hinge between the base member and the cover member;
(e) a testing element fixed to the base member and a testing element fixed to the cover member, at least one of the testing elements including an elongated chromatographic medium, and wherein one of the testing elements is arranged for receiving fluid and for transferring the fluid to the testing element having the chromatographic medium, whereby the fluid is arranged to traverse the chromatographic medium along a defined flow path; and
(f) closure means comprising interrupted beveled edges on the cover member, the interrupted beveled edges being supplementary to the undercut edges and being adapted to be received and retained in a closed position with the undercut edges of the fixed members in an edge-to-edge engagement, the base member, the cover member, and the fixed members being formed of a sufficiently rigid material to minimize bowing on the closure, and thereby to ensure that, together with the hinge between the base member and the cover member, and with the closure means, the closure force is substantially equally distributed along the length of the closure means whereby when the beveled edges are in the closed position, a closure force is distributed substantially uniformly between the cover member and the fixed members such that fluid is effectively transferred between the testing elements and is enabled to effectively traverse the chromatographic medium; wherein the beveled edges are interrupted with at least one uncut bridge region to increase the force required to separate the base member and the cover member.

79. The testing device of claim 78 wherein the defined flow path is from a first end of the chromatographic medium to a second end of the chromatographic medium.

80. The testing device of claim 78 wherein the defined flow path is from a point removed from both a first end and a second end of the chromatographic medium toward both the first end and the second end of the chromatographic medium.

81. The testing device of claim 78 further including a window located in at least one of the base member and the cover member, the window being aligned along the length of the chromatographic medium such that a test indication on a chromatographic medium is visible through the window when the base member and the cover member are in a closed position.

82. The testing device of claim 78 wherein the base member and the cover member are formed from the same board material element and the hinge includes at least one crease formed in the board material, the board material having a thickness of about 0.024 inches.

83. The testing device of claim 78 wherein the base member and the cover member are planar elements formed from the same material element having a thickness and the hinge is formed along a crease line in the material and the test elements are located in adjacency on the covered member and the base member and the fixed members are mounted on a position of the base member, such that in a position of closure the covered portion overlies the portion of the base member not occupied by the fixed members, and the cover member and fixed members have edges in abutment, and wherein inward force applied by the cover member and the base member on the test elements toward each other is effected uniformly when the edge of the fixed member and the edge of the cover member are in the edge-to-edge engagement.

84. The testing device of claim 78 wherein the interrupted bevel closure includes at least two bridges.

85. The testing device of claim 84 wherein the bridges are located in a region that spans substantially less that the entire contact area between the cover member and the fixed members.

86. The testing device of claim 84 wherein the bridges are located in a region that spans substantially the entire contact area between the cover member and the fixed members.

87. The testing device of claim 78 wherein the angle of the bevel is between about 5 degrees to about 30 degrees from the vertical.

88. The testing device of claim 87 wherein the angle of the bevel is from about 6 degrees to about 15 degrees from the vertical.

89. The testing device of claim 88 wherein the angle of the bevel is between about 8 degrees to about 10 degrees from the vertical.

90. A reclosable testing device comprising:
(a) a base member;
(b) a cover member having an interrupted beveled edge, the interrupted beveled edge including an exposed line of engagement;
(c) a fixed member fixed to the base member, the fixed member having an undercut edge being supplementary to the interrupted beveled edge and including an exposed line of engagement;
(d) a hinge between the base member and the cover member; and
(e) a testing element fixed to the base member and a testing element fixed to the cover member, at least one of the testing elements being arranged for receiving fluid and for transferring fluid to the other testing element; closure of the cover member on the base member effecting engagement of the interrupted beveled edge with the undercut edge of the fixed member, the interrupted beveled edge being adapted to be received and retained in a closed position in a edge-to-edge engagement with the undercut edge of the fixed member, forming a means for closure, the base member, the cover member and the fixed member being formed of a sufficiently rigid material to minimize bowing on the closure thereby to ensure that a sample for testing and one of the testing elements come into operable contact for effecting a test, and that a force is distributed substantially evenly over the cover member and thereby further ensuring that, together with the hinge between the base member and the cover member, and with the closure means formed by closure of the cover member on the base member, the closure force is substantially equally distributed along the length of the closure means; and wherein the beveled edge is interrupted with at least one uncut bridge region to increase the force required to separate the base member and the cover member.

91. The testing device of claim 90 wherein the base member and the cover member are formed from the same board material element and the hinge includes at least one crease formed in the board material, the board material having a thickness of about 0.024 inches.

92. The testing device of claim 90 wherein the base member and the cover member are planar elements formed from a same material element having a thickness and the hinge is formed along the crease line in the material, and the test elements are located in adjacency on the cover member and the base member and the fixed member is mounted on a portion of the base member, such that in a position of closure, the covered portion overlies the portion of the base member not occupied by the fixed member, and the cover member and fixed member have edges in abutment, and wherein an inward force applied by the cover member and the base member on the test elements toward each other is effected uniformly when the edges of the fixed member and the edges of the cover member are in the edge-to-edge engagement.

93. The testing device of claim 90 wherein one of the testing element fixed to the base member and the testing element fixed to the cover member includes a chromatographic medium.

94. The testing device of claim 90 wherein the interrupted beveled edge includes at least two bridges.

95. The testing device of claim 94 wherein the bridges are located in a region that spans substantially less than the entire contact area between the cover member and the fixed member.

96. The testing device of claim 94 wherein the bridges are located in a region that spans substantially the entire contact area between the cover member and the fixed member.

97. The testing device of claim 90 wherein the angle of the bevel is between about 5 degrees to about 30 degrees from the vertical.

98. The testing device of claim 97 wherein the angle of the bevel is from about 6 degrees to about 15 degrees from the vertical.

99. The testing device of claim 98 wherein the angle of the bevel is from about 8 degrees to about 10 degrees from the vertical.

100. A reclosable testing device comprising:
(a) a base member;
(b) a cover member having interrupted beveled edges, the interrupted beveled edges including exposed lines of engagement;

(c) fixed members fixed to the base member, each of the fixed members having undercut edges, the undercut edges being supplementary to the interrupted beveled edges and including exposed lines of engagement;

(d) a hinge between the base member and the cover member; and (e) a testing element fixed to the base member and a testing element fixed to the cover member, at least one of the testing elements being arranged for receiving fluid and for transferring fluid to the other testing element; closure of the cover member on the base member effecting engagement of the interrupted beveled edges to be received and retained in edge-to-edge contact in the closed position forming means for closing with the undercut edges of the fixed members and the exposed lines of engagement of the interrupted beveled edges and the undercut edges respectively being substantially flush to the fixed members and to the cover member; the base member, the cover member, and the fixed members being formed of a sufficiently rigid material to minimize bowing on the closure thereby to ensure that a sample for testing and one of the testing elements come into operable contact for effecting a test, and that a force is distributed substantially evenly over the cover member and thereby further insuring that, together with the hinge between the base member and the cover member, and with the means for closing formed by closure of the cover member on the base member, the closure force is substantially equally distributed along the length of the closure means, wherein the beveled edge is interrupted with at least one uncut bridge region to increase the force required to separate the base member and the cover member.

101. The testing device of claim 100 wherein the base member and the cover member are formed from the same board material element and the hinge includes at least one crease formed in the board material, the board material having a thickness of about 0.024 inches.

102. The testing device of claim 100 wherein the base member and the cover member are planar elements formed from a same material element having a thickness and the hinge is formed along a crease line in the material and the test elements are located in adjacency on the cover member and the base member and the fixed members are mounted on a portion of the base member, such that in a position of closure, the covered portion overlies the portion of the base member not occupied by the fixed members, and the cover member and fixed members have edges in abutment, and wherein an inward force applied by the cover member and the base member on the test elements toward each other is effected uniformly when the edge of the fixed members and the edge of the cover member are in the edge-to-edge engagement.

103. The testing device of claim 100 wherein one of the testing element fixed to the base member and the testing element fixed to the cover member includes a chromatographic medium thereon.

104. The testing device of claim 100 wherein the interrupted beveled edge includes at least two bridges.

105. The testing device of claim 104 wherein the bridges are located in a region that spans substantially less than the entire contact area between the cover member and the fixed members.

106. The testing device of claim 104 wherein the bridges are located in a region that spans substantially the entire contact area between the cover member and the fixed member.

107. The testing device of claim 100 wherein the angle of the bevel is between from about 5 degrees to about 30 degrees from the vertical.

108. The testing device of claim 107 wherein the angle of the bevel is from about 6 degrees to about 15 degrees from the vertical.

109. The testing device of claim 108 wherein the angle of the bevel is from about 8 degrees to about 10 degrees from the vertical.

* * * * *